United States Patent
Jiang et al.

(10) Patent No.: US 11,028,173 B2
(45) Date of Patent: Jun. 8, 2021

(54) ANTI-PD-1 ANTIBODIES

(71) Applicant: Shanghai Henlius Biotech Inc., Shanghai (CN)

(72) Inventors: Weidong Jiang, Freemont, CA (US); Pei-Hua Lin, Fremont, CA (US); Chi-Ling Tseng, Taipei (TW)

(73) Assignee: Shanghai Henlius Biotech, Inc., Shanghai (CN)

( * ) Notice: Subject to any disclaimer, the term of this patent is extended or adjusted under 35 U.S.C. 154(b) by 0 days.

(21) Appl. No.: 16/352,194

(22) Filed: Mar. 13, 2019

(65) Prior Publication Data

US 2019/0218295 A1  Jul. 18, 2019

Related U.S. Application Data

(63) Continuation of application No. PCT/US2017/050851, filed on Sep. 9, 2017.

(60) Provisional application No. 62/519,590, filed on Jun. 14, 2017, provisional application No. 62/395,832, filed on Sep. 16, 2016.

(51) Int. Cl.
*A61K 39/00* (2006.01)
*C07K 16/28* (2006.01)
*A61K 51/10* (2006.01)
*A61K 47/68* (2017.01)
*A61P 35/00* (2006.01)
*C07K 16/22* (2006.01)
*G01N 33/574* (2006.01)
*A61K 49/00* (2006.01)

(52) U.S. Cl.
CPC ...... *C07K 16/2818* (2013.01); *A61K 47/6849* (2017.08); *A61K 49/0058* (2013.01); *A61K 51/1027* (2013.01); *A61P 35/00* (2018.01); *C07K 16/22* (2013.01); *G01N 33/57492* (2013.01); *A61K 2039/505* (2013.01); *A61K 2039/507* (2013.01); *A61K 2039/545* (2013.01); *C07K 16/2863* (2013.01); *C07K 2317/14* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
CPC ............... C07K 16/2818; C07K 16/22; C07K 16/2863; A61K 51/1027; A61K 49/0058; A61P 35/00
See application file for complete search history.

(56) References Cited

U.S. PATENT DOCUMENTS

| | | | |
|---|---|---|---|
| 2013/0136735 | A1 | 5/2013 | Truneh et al. |
| 2016/0159905 | A1 | 6/2016 | Abdiche et al. |
| 2016/0200815 | A1 | 7/2016 | Feldman et al. |
| 2017/0247454 | A1 | 8/2017 | Benz et al. |

FOREIGN PATENT DOCUMENTS

| | | |
|---|---|---|
| WO | 2010022737 | 3/2010 |
| WO | 2016077397 | 5/2016 |

OTHER PUBLICATIONS

Strome et al., The Oncologist, 2007; 12:1084-95 (Year: 2007).*
Brand et al., Anticancer Res. 2006; 26:463-70 (Year: 2006).*
International Search Report for PCT Patent Application No. PCT/US2017/050851. (2017).
European Search Report dated Mar. 13, 2020 For European Patent Application No. 17851358.6.

* cited by examiner

*Primary Examiner* — Sheela J. Huff
(74) *Attorney, Agent, or Firm* — Thomas Horstemeyer, LLP

(57) ABSTRACT

Provided are anti-PD-1 antibodies, and antigen binding fragments thereof. Also provided are isolated nucleic acid molecules that encode the anti-PD-1 antibodies or antigen binding fragments thereof, related expression vectors, and host cells. Provided are methods of making anti-PD-1 antibodies, and antigen binding fragments thereof. Also provided are related pharmaceutical compositions and methods of their use to treat subjects. This abstract is intended as a scanning tool for purposes of searching in the particular art and is not intended to be limiting of the present disclosure.

18 Claims, 23 Drawing Sheets

Specification includes a Sequence Listing.

Figure 8A

```
              1                                                        50
    c1G4_LC   QLEDIVMTQS HKFMSTSVGD RVSITCKASQ DVTTAVAWYQ QKPGQSPKLL
    h1G4_LC   ...DIQMTQS PSSLSASVGD RVTITCKASQ DVTTAVAWYQ QKPGKAPKLL
 IGKV1-39-01  ...DIQMTQS PSSLSASVGD RVTITCRASQ SISSYLNWYQ QKPGKAPKLL
     NIV_LC   ...EIVLTQS PATLSLSPGE RATLSCRASQ SVSSYLAWYQ QKPGQAPRLL 51                                                       100
    c1G4_LC   IYWASTRHTG VPDRFTGSGS GTDYTLTINS VQAEDLALYY CQQHYTIPWT
    h1G4_LC   IYWASTRHTG VPSRFSGSGS GTDFTLTISS LQPEDFATYY CQQHYTIPWT
 IGKV1-39-01  IYAASSLQSG VPSRFSGSGS GTDFTLTISS LQPEDFATYY CQQSYSTP..
     NIV_LC   IYDASNRATG IPARFSGSGS GTDFTLTISS LEPEDFAVYY CQQSSNWPRT 101                                                      150
    c1G4_LC   FGGGTKLEIK RTVAAPSVFI FPPSDEQLKS GTASVVCLLN NFYPREAKVQ
    h1G4_LC   FGGGTKLEIK RTVAAPSVFI FPPSDEQLKS GTASVVCLLN NFYPREAKVQ
 IGKV1-39-01  .......... .......... .......... .......... ..........
     NIV_LC   FGQGTKVEIK RTVAAPSVFI FPPSDEQLKS GTASVVCLLN NFYPREAKVQ 151                                                      200
    c1G4_LC   WKVDNALQSG NSQESVTEQD SKDSTYSLSS TLTLSKADYE KHKVYACEVT
    h1G4_LC   WKVDNALQSG NSQESVTEQD SKDSTYSLSS TLTLSKADYE KHKVYACEVT
 IGKV1-39-01  .......... .......... .......... .......... ..........
     NIV_LC   WKVDNALQSG NSQESVTEQD SKDSTYSLSS TLTLSKADYE KHKVYACEVT 201        217
    c1G4_LC   HQGLSSPVTK SFNRGEC
    h1G4_LC   HQGLSSPVTK SFNRGEC
 IGKV1-39-01  .......... .......
     NIV_LC   HQGLSSPVTK SFNRGEC
```

Figure 8B

```
                   1                                                            50
        c1G4_HC    EVMLVESGGG LVKPGGSLKL SCAASGFTFS NYGMSWVRQT PEKSLEWVAT
        h1G4_HC    QVQLVESGGG LVKPGGSLRL SCAASGFTFS NYGMSWIRQA PGKGLEWVST
     IGHV3-11-04   QVQLVESGGG LVKPGGSLRL SCAASGFTFS DYYMSWIRQA PGKGLEWVSY
         NIV_HC    QVQLVESGGG VVQPGRSLRL DCKASGITFS NSGMHWVRQA PGKGLEWVAV 51                                                           100
        c1G4_HC    ISGGGSNIYY PDSVKGRFTI SRDNAKNNLF LQMSGLRSED TALYYCVSYY
        h1G4_HC    ISGGGSNIYY ADSVKGRFTI SRDNAKNSLY LQMNSLRAED TAVYYCVSYY
     IGHV3-11-04   ISSSGSTIYY ADSVKGRFTI SRDNAKNSLY LQMNSLRAED TAVYYCAR..
         NIV_HC    IWYDGSKRYY ADSVKGRFTI SRDNSKNTLF LQMNSLRAED TAVYYCATN.

101                                                          150
        c1G4_HC    YGIDFWGQGT SVTVSSASTK GPSVFPLAPC SRSTSESTAA LGCLVKDYFP
        h1G4_HC    YGIDFWGQGT SVTVSSASTK GPSVFPLAPC SRSTSESTAA LGCLVKDYFP
     IGHV3-11-04   .......... .......... .......... .......... ..........
         NIV_HC    ..DDYWGQGT LVTVSSSTK. GPSVFPLAPC SRSTSESTAA LGCLVKDYFP 151                                                          200
        c1G4_HC    EPVTVSWNSG ALTSGVHTFP AVLQSSGLYS LSSVVTVPSS SLGTKTYTCN
        h1G4_HC    EPVTVSWNSG ALTSGVHTFP AVLQSSGLYS LSSVVTVPSS SLGTKTYTCN
     IGHV3-11-04   .......... .......... .......... .......... ..........
         NIV_HC    EPVTVSWNSG ALTSGVHTFP AVLQSSGLYS LSSVVTVPSS SLGTKTYTCN 201                                                          250
        c1G4_HC    VDHKPSNTKV DKRVESKYGP PCPPCPAPEF LGGPSVFLFP PKPKDTLMIS
        h1G4_HC    VDHKPSNTKV DKRVESKYGP PCPPCPAPEF LGGPSVFLFP PKPKDTLMIS
     IGHV3-11-04   .......... .......... .......... .......... ..........
         NIV_HC    VDHKPSNTKV DKRVESKYGP PCPPCPAPEF LGGPSVFLFP PKPKDTLMIS 251                                                          300
        c1G4_HC    RTPEVTCVVV DVSQEDPEVQ FNWYVDGVEV HNAKTKPREE QFNSTYRVVS
        h1G4_HC    RTPEVTCVVV DVSQEDPEVQ FNWYVDGVEV HNAKTKPREE QFNSTYRVVS
     IGHV3-11-04   .......... .......... .......... .......... ..........
         NIV_HC    RTPEVTCVVV DVSQEDPEVQ FNWYVDGVEV HNAKTKPREE QFNSTYRVVS 301                                                          350
        c1G4_HC    VLTVLHQDWL NGKEYKCKVS NKGLPSSIEK TISKAKGQPR EPQVYTLPPS
        h1G4_HC    VLTVLHQDWL NGKEYKCKVS NKGLPSSIEK TISKAKGQPR EPQVYTLPPS
     IGHV3-11-04   .......... .......... .......... .......... ..........
         NIV_HC    VLTVLHQDWL NGKEYKCKVS NKGLPSSIEK TISKAKGQPR EPQVYTLPPS 351                                                          400
        c1G4_HC    QEEMTKNQVS LTCLVKGFYP SDIAVEWESN GQPENNYKTT PPVLDSDGSF
        h1G4_HC    QEEMTKNQVS LTCLVKGFYP SDIAVEWESN GQPENNYKTT PPVLDSDGSF
     IGHV3-11-04   .......... .......... .......... .......... ..........
         NIV_HC    QEEMTKNQVS LTCLVKGFYP SDIAVEWESN GQPENNYKTT PPVLDSDGSF 401                                                          443
        c1G4_HC    FLYSRLTVDK SRWQEGNVFS CSVMHEALHN HYTQKSLSLS LGK
        h1G4_HC    FLYSRLTVDK SRWQEGNVFS CSVMHEALHN HYTQKSLSLS LGK
     IGHV3-11-04   .......... .......... .......... .......... ...
         NIV_HC    FLYSRLTVDK SRWQEGNVFS CSVMHEALHN HYTQKSLSLS LGK
```

ANTI-PD-1 ANTIBODIES

CROSS-REFERENCE TO RELATED APPLICATIONS

This application is a continuation of a PCT International Application No. PCT/US2017/050851, filed on Sep. 9, 2017, which claims the benefit and priority to U.S. Provisional Patent Application No. 62/395,832, which was filed on Sep. 16, 2016, and U.S. Provisional Patent Application No. 62/519,590, which was filed on Jun. 14, 2017. The contents of each of these applications are hereby incorporated by reference.

REFERENCE TO A SEQUENCE LISTING SUBMITTED AS A TEXT FILE VIA EFS-WEB

The Sequence Listing submitted Mar. 12, 2019 as a text file named "000020_000004PCT-LF_.txt," created on Sep. 19, 2017, and having a size of 40,346 bytes is hereby incorporated by reference pursuant to 37 C.F.R. § 1.52(e)(5).

FIELD OF THE INVENTION

The invention relates generally to anti-PD-1 antibodies, and methods of use thereof, in the treatment of human cancers.

BACKGROUND OF THE INVENTION

Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., 2000; Latchman et al., 2001). Unlike CTLA-4, PD-1 primarily functions in peripheral tissues where activated T-cells may encounter the immunosuppressive PD-L1 (B7-H1) and PD-L2 (B7-DC) ligands expressed by tumor and/or stromal cells (Flies et al., 2011; Topalian et al., 2012a). Inhibition of the PD-1/PD-L1 interaction mediates potent antitumor activity in preclinical models (U.S. Pat. Nos. 8,008,449 and 7,943,743), and the use of Ab inhibitors of the PD-1/PD-L1 interaction for treating cancer has entered clinical trials (Brahmer et al., 2010; Flies et al., 2011; Topalian et al., 2012b; Brahmer et al., 2012).

There exists a need for the development of anticancer therapeutics directed against PD-1. The present invention meets this and other needs.

SUMMARY OF THE INVENTION

Provided by the invention are anti-PD-1 antibodies and/or antigen binding fragments thereof. In certain embodiments, the anti-PD-1 antibody of the invention is a chimeric anti-PD-1 antibody c1G4 and/or humanized anti-PD-1 h1G4, comprising a light chain (LC) variable domain sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14).

The invention further provides affinity matured antibodies against humanized h1G4 anti-PD-1 antibody. In certain embodiments, the matured anti-PD-1 antibody (e.g., anti-PD-1 antibody, 33B) of the invention comprises a light chain (LC) variable domain sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain (HC) variable domain sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20).

In other embodiments, the matured anti-PD-1 antibody (e.g., anti-PD-1 antibody, 66E) of the invention comprises a light chain (LC) variable domain sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23).

In certain embodiments, the matured anti-PD-1 antibody (e.g., anti-PD-1 antibody, 711D) of the invention comprises a light chain (LC) variable domain sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

The sequences of the CDRs noted herein are provided in Table 1 below.

TABLE 1

| SEQ ID NO: 9 | KASQDVTTAVA |
|---|---|
| SEQ ID NO: 10 | WASTRHT |
| SEQ ID NO: 11 | QQHYTIPWT |
| SEQ ID NO: 12 | FTFSNYGMS |
| SEQ ID NO: 13 | TISGGGSNIY |
| SEQ ID NO: 14 | VSYYYGIDF |
| SEQ ID NO: 15 | KASTDVTTAVA |
| SEQ ID NO: 16 | WASLRHT |
| SEQ ID NO: 17 | QQHYGIPWT |

TABLE 1-continued

| | |
|---|---|
| SEQ ID NO: 18 | FRFSNYGMS |
| SEQ ID NO: 19 | TISGGGSNAY |
| SEQ ID NO: 20 | TSYYYGIDF |
| SEQ ID NO: 21 | KAKQDVTTAVA |
| SEQ ID NO: 22 | QQHYWIPWT |
| SEQ ID NO: 23 | VSYYYGIDL |
| SEQ ID NO: 24 | KASQDVTNAVA |
| SEQ ID NO: 25 | SSYYYGIDL |

In some embodiments, the anti-PD-1 antibody comprises a light chain (LC) variable domain sequence comprising (1) a CDR-L1 comprising an amino acid sequence selected from the group consisting of SEQ ID Nos: 9, 21 and 24; (2) a CDR-L2 comprising an amino acid sequence of SEQ ID Nos: 10 or 16; (3) a CDR-L3 comprising an amino acid sequence selected from the group consisting of SEQ ID Nos: 11, 17, 22, and a heavy chain (HC) variable domain sequence comprising (1) a CDR-H1 comprising an amino acid sequence of SEQ ID Nos: 12 or 18; (2) a CDR-H2 comprising an amino acid sequence of SEQ ID Nos: 13 or 19; and (3) a CDR-H3 comprising an amino acid sequence selected from the group consisting of SEQ ID Nos: 14, 20, 23, and 25.

Also provided by the invention is an anti-PD-1 antibody or antigen binding fragment thereof, comprising a heavy chain sequence comprising the amino acid sequence set forth in (SEQ ID NO:4) and a light chain sequence comprising the amino acid sequence set forth in SEQ ID NO:2).

Also provided by the invention is a humanized anti-PD-1 antibody or antigen binding fragment thereof, comprising the amino acid sequence set forth in (SEQ ID NO:8) and a light chain sequence comprising the amino acid sequence set forth in SEQ ID NO:6).

In some embodiments according to (or as applied to) any of the embodiments above, the antibody comprises an Fc sequence of a human IgG. In some embodiments according to (or as applied to) any of the embodiments above, the antigen binding fragment is selected from the group consisting of a Fab, Fab', a F(ab)'2, a single-chain Fv (scFv), an Fv fragment, a diabody, and a linear antibody. In some embodiments according to (or as applied to) any of the embodiments above, the antibody is a multispecific antibody.

In some embodiments according to (or as applied to) any of the embodiments above, the anti-PD-1 antibody or antigen binding fragment thereof is conjugated to a therapeutic agent. In some embodiments according to (or as applied to) any of the embodiments above, the anti-PD-1 antibody or antigen binding fragment thereof is conjugated to a label. In some embodiments according to (or as applied to) any of the embodiments above, the label is selected from the group consisting of a radioisotope, a fluorescent dye, and an enzyme.

The invention provides an isolated nucleic acid molecule that encodes the anti-PD-1 antibody or antigen binding fragment thereof according to (or as applied to) any of the embodiments above. Also provided is an expression vector encoding the nucleic acid molecule according to (or as applied to) any of the embodiments above. Cells comprising the expression vector according to (or as applied to) any of the embodiments above are also provided. The invention also provides a method of producing an antibody comprising culturing a cell according to (or as applied to) any of the embodiments above and recovering the antibody or antigen-binding fragment thereof from the cell culture. In some embodiments according to (or as applied to) any of the embodiments above, the cell is a mammalian cell. In some embodiments according to (or as applied to) any of the embodiments above, the mammalian cell is a CHO cell. In some embodiments according to (or as applied to) any of the embodiments above, the cell is a stable mammalian cell line. In some embodiments according to (or as applied to) any of the stable mammalian cell line is a CHO cell line.

The invention provides a composition comprising the anti-PD-1 antibody or antigen binding fragment thereof according to (or as applied to) any of the embodiments above and a pharmaceutically acceptable carrier.

The invention provides a method of detecting a PD-1 protein in sample from a patient by contacting the anti-PD-1 antibody or antigen binding fragment thereof according to (or as applied to) any of the embodiments above to the sample and detecting the anti-PD-1 antibody bound to the PD-1 protein. In some embodiments according to (or as applied to) any of the embodiments above, the anti-PD-1 antibody or antigen binding fragment thereof is used an immunohistochemistry assay (IHC) or in an ELISA assay.

Also provided is a method of treating cancer in a subject, comprising administering an effective amount of the composition according to (or as applied to) any of the embodiments above to the subject. Also provided is a composition comprising an anti-PD-1 antibody or antigen binding fragment thereof according to (or as applied to) any of the embodiments above for use in the treatment of cancer. Provided is the use of an anti-PD-1 antibody or antigen binding fragment thereof according to (or as applied to) any of the embodiments above in the manufacture of a medicament for treating cancer. In some embodiments according to (or as applied to) any of the embodiments above, the cancer is selected from melanoma, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer and non-small cell lung cancer (NSCLC), esophageal cancer, nasopharyngeal carcinoma (NPC), biliary tract cancer, colorectal cancer, cervical cancer, thyroid cancer, and salivary cancer. In some embodiments, according to (or as applied to) any of the embodiments above, the subject is further administered a therapeutic agent selected from the group consisting of an anti-neoplastic agent, a chemotherapeutic agent, a growth inhibitory agent and a cytotoxic agent. In some embodiments, according to (or as applied to) any of the embodiments above, the subject is further administered radiation therapy. In some embodiments, according to (or as applied to) any of the embodiments above, the subject is further administered a therapeutic antibody against VEGF, VEGFR2, or EGFR.

BRIEF DESCRIPTION OF THE DRAWINGS

FIG. 1A shows the results of ELISAs performed to compare the binding of anti-PD-1 antibodies c1G4 and referenced anti-PD-1 to PD-1-His. FIG. 1B shows the results of a second set of ELISAs performed to compare the binding of anti-PD-1 antibodies c1G4 and referenced anti-PD-1 to PD-1-AP. The data indicate that c1G4 and referenced anti-PD-1 are able to bind to both PD-1-His and PD-1-AP.

FIG. 2A shows the results of ELISAs performed to compare the ability of anti-PD-1 antibodies c1G4 and referenced anti-PD-1 to block binding of PD-L1 and PD-1. Both c1G4 and the referenced anti-PD-1 were found to block the binding of PD-L1 to PD-1. FIG. 2B shows the results of ELISAs performed to determine the ability of anti-PD-1 antibody c1G4 to compete with the referenced anti-PD-1 for binding to PD-1-His. The data indicate that both c1G4 and the referenced anti-PD-1 are able to block the binding of PD-L1 to PD-1, and c1G4 is able to compete with anti-PD-1 ref for binding to PD-1-His.

FIG. 5A illustrates a bar graph showing concentration dependent IL-2 secretion; FIG. 5B illustrates a bar graph showing concentration dependent IFN-γ secretion.

FIG. 6A illustrates a bar graph showing the $CD4^+$ T cell proliferation at various concentration of antibodies; FIG. 6B illustrates a bar graph showing the $CD8^+$ T cell proliferation at various concentration of antibodies.

FIGS. 8A-8B. Sequence alignment for c1G4 and h1G4. FIG. 8A shows an amino acid sequence alignment of the light chains of c1G4, humanized h1G4, human germline light chain variable region IGKV1-39*01, and Nivolumab (NIV) (SEQ ID NOS 27-30, respectively, in order of appearance). FIG. 8B shows an amino acid sequence alignment of the heavy chains of c1G4, humanized h1G4, human germline heavy chain variable region IGHV3-11*04, and Nivolumab (NIV) (SEQ ID NOS 31-34, respectively, in order of appearance). The CDRs (Complementary Determining Regions) grafted from c1G4 for humanization were marked in bold and underlined text.

FIG. 13A illustrates a bar graph showing concentration dependent IL-2 secretion; FIG. 13B illustrates a bar graph showing concentration dependent IFN-γ secretion.

FIG. 14A illustrates a bar graph showing the $CD4^+$ T cell proliferation at various concentration of antibodies; FIG. 14B illustrates a bar graph showing the $CD8^+$ T cell proliferation at various concentration of antibodies.

FIG. 19A illustrates a bar graph showing concentration dependent IL-2 secretion; FIG. 19B illustrates a bar graph showing concentration dependent IFN-γ secretion.

DETAILED DESCRIPTION OF THE INVENTION

Figure 1A:
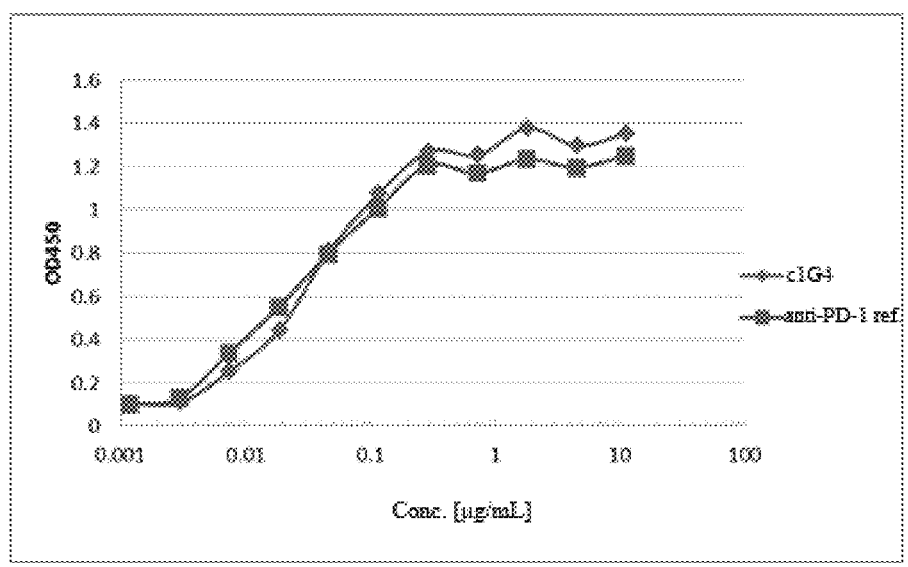
FIGS. 1A-1B. Binding of c1G4 to PD-1 recombinant protein.

The present invention provides novel anti-PD-1 antibodies and/or antigen binding fragments thereof. The inventors have surprisingly found that the anti-PD-1 antibodies, e.g., chimeric c1G4 and humanized h1G4 antibodies described herein, as well as their affinity matured antibodies, e.g. 33B, 66E, and 711D, enhance the secretion of IL-2 and IFNγ by T cells and proliferation of CD4+ and CD8+ T cells. The anti-PD-1 antibodies described herein also exhibit enhanced efficacy and/or anti-tumor activities as compared to OPDIVO® (Nivolumab), an FDA-approved humanized IgG4 anti-PD-1 monoclonal antibody used to treat cancer.

Also provided are immunoconjugates, nucleic acids encoding the novel anti-PD-1 antibodies described herein, and compositions (such as pharmaceutical compositions). The invention also provides methods of using novel anti-PD-1 antibodies to detect PD-1 in a sample (such as an in vivo or ex vivo sample), compositions comprising such antibodies for use in treating cancer, and uses of such antibodies in the manufacture of a medicament for the treatment of cancer.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

The term "adjuvant therapy" refers to treatment given after the primary therapy, usually surgery. Adjuvant therapy for cancer or disease may include immune therapy, chemotherapy, radiation therapy, or hormone therapy.

The term "maintenance therapy" refers to scheduled retreatment that is given to help maintain a previous treatment's effects. Maintenance therapy is often given to help keep cancer in remission or prolong a response to a specific therapy regardless of disease progression.

The term "invasive cancer" refers to cancer that has spread beyond the layer of tissue in which it started into the normal surrounding tissues. Invasive cancers may or may not be metastatic.

The term "non-invasive cancer" refers to a very early cancer or a cancer that has not spread beyond the tissue of origin.

The term "progression-free survival" in oncology refers to the length of time during and after treatment that a cancer does not grow. Progression-free survival includes the amount of time patients have experienced a complete response or a partial response, as well as the amount of time patients have experienced stable disease.

The term "progressive disease" in oncology can refer to a tumor growth of more than 20 percent since treatment began—either due to an increase in mass or a spread in the tumor.

A "disorder" is any condition that would benefit from treatment with the antibody. For example, mammals who suffer from or need prophylaxis against abnormal PD-1 activity. This includes chronic and acute disorders or diseases including those pathological conditions which predispose the mammal to the disorder in question. Non-limiting examples of disorders to be treated herein include cancer (such as head and neck cancer, throat cancer, colorectal cancer, lung cancer, etc.).

"Tumor", as used herein, refers to all neoplastic cell growth and proliferation, whether malignant or benign, and all pre-cancerous and cancerous cells and tissues.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one which can specifically bind to PD-1. In one embodiment, the antibody can prevent or substantially reduce the ability of PD-1 to induce cell proliferation.

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

As used herein, the term "CDR" or "complementary determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 2 as a comparison.

TABLE 2

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al. Nature. 256:495 (1975), or can be made using recombinant DNA methods in bacterial, eukaryotic animal or plant cells (see, e.g., U.S. Pat. No. 4,816,567). The "monoclonal antibodies" can also be isolated from phage antibody libraries using the techniques described in Clackson et al., Nature, 352:624-628 (1991), Marks et al., J. Mol. Biol., 222:581-597 (1991), and the Examples below, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062, (1995)); single-chain antibody molecules; and multispecific antibodies formed from antibody fragments. The expression "linear antibodies" generally refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by di sulfides. The effector functions of antibodies are determined by sequences in the Fc region, which region is also the part recognized by Fc receptors (FcR) found on certain types of cells.

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

The term "Fc region-comprising polypeptide" refers to a polypeptide, such as an antibody or immunoadhesin (see definitions elsewhere herein), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this invention can comprise polypeptides populations with all K447 residues removed, polypeptide populations with no K447 residues removed or polypeptide populations having a mixture of polypeptides with and without the K447 residue.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Kabat et al., Sequences of Immunological Interest. 5th Ed. Public Health Service, National Institutes of Health, Bethesda, Md. (1991)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody.

However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, N.Y., pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues.

Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The terms "Fc receptor" or "FcR" are used to describe a receptor that binds to the Fc region of an antibody. In one embodiment, an FcR of this invention is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, Annu. Rev. Immunol 9:457-92 (1991); Capel et al., Immunomethods 4:25-34 (1994); and de Haas et al. J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

The term "FcRn" refers to the neonatal Fc receptor (FcRn). FcRn is structurally similar to major histocompatibility complex (MHC) and consists of a α-chain noncovalently bound to β2-microglobulin. The multiple functions of the neonatal Fc receptor FcRn are reviewed in Ghetie and Ward (2000) Annu. Rev. Immunol. 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec Immunol. 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain. An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3-fold, preferably about 5-, 10-, 25-, 50-, 60-, 100-, 150-, 200-, up to 500-fold, or about 25% to 1000% improvement in binding. The polypeptide variant which "exhibits decreased binding" to an FcR, binds at least one FcR with lower affinity (e.g., higher apparent Kd or higher IC50 value) than a parent polypeptide. The decrease in binding compared to a parent polypeptide may be about 40% or more decrease in binding. "Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In one embodiment, the preferred variant is from about 5-fold to about 100-fold, e.g. from about 25- to about 50-fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. J. Immunol. 164: 4178-4184 (2000).

An "effective amount" of an anti-PD-1 antibody (or fragment thereof) or composition as disclosed herein is an amount sufficient to carry out a specifically stated purpose. An "effective amount" can be determined empirically and by known methods relating to the stated purpose. The term "therapeutically effective amount" refers to an amount of an anti-PD-1 antibody (or fragment thereof) or composition as disclosed herein, effective to "treat" a disease or disorder in a mammal (aka patient). In the case of cancer, the therapeutically effective amount of the anti-PD-1 antibody (or fragment thereof) or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-PD-1 antibody (or fragment thereof) or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "growth inhibitory amount" of an anti-PD-1 antibody (or fragment thereof) or composition as disclosed herein of this invention is an amount capable of inhibiting the growth of a cell, especially tumor, e.g., cancer cell, either in vitro or in vivo. A "growth inhibitory amount" of a polypeptide, antibody, antagonist or composition of this invention for purposes of inhibiting neoplastic cell growth can be determined empirically and by known methods or by examples provided herein.

A "cytotoxic amount" of an anti-PD-1 antibody (or fragment thereof) or composition of this invention is an amount capable of causing the destruction of a cell, especially tumor, e.g., cancer cell, either in vitro or in vivo. A "cytotoxic amount" of an anti-PD-1 antibody (or fragment thereof) or composition of this invention for purposes of inhibiting neoplastic cell growth can be determined empirically and by methods known in the art.

A "growth inhibitory amount" of an anti-PD-1 antibody (or fragment thereof) or composition of this invention is an amount capable of inhibiting the growth of a cell, especially tumor, e.g., cancer cell, either in vitro or in vivo. A "growth inhibitory amount" of an anti-PD-1 antibody (or fragment thereof) or composition of this invention for purposes of inhibiting neoplastic cell growth can be determined empirically and by known methods or by examples provided herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as PD-1). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of PD-1 gene product, mRNA molecules, or a PD-1 polypeptide; a change in the levels of a PD-1 polypeptide or amount bound to a target; a change in biological function/activity of a PD-1 polypeptide. In some embodiments, "detecting" may include detecting wild type PD-1 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Anti-PD-1 Antibodies

The present invention is based on the identification of novel antibodies that bind PD-1 receptor (PD-1). The anti-PD-1 antibodies can be used in a variety of therapeutic and diagnostic methods. For example, the anti-PD-1 antibodies can be used alone or in combination with other agents in treating disease characterized by abnormal PD-1 expression or abnormal PD-1 activity, including, e.g., melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer. The antibodies provided herein can also be used for detecting PD-1 protein in patients or patient samples by administering the anti-PD-1 antibodies to patients and detecting the anti-PD-1 antibody bound to the PD-1 protein in a sample from the patient (e.g., in vivo or ex vivo) or by contacting the anti-PD-1 antibodies with samples from patients and detecting qualitatively or quantitatively the anti-PD-1 antibody bound to the PD-1 protein.

Programmed cell death protein 1 (also known as PD-1 and CD279 (cluster of differentiation 279)), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2. PD-1, functioning as an immune checkpoint, plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

An anti-PD-1 antibody is an antibody that binds to PD-1 with sufficient affinity and specificity. Preferably, an anti-PD-1 antibody provided herein (or the antigen-binding fragment thereof) can be used as a therapeutic agent in targeting and interfering with diseases or conditions wherein the PD-1 activity is involved. An anti-PD-1 antibody will usually not bind to other immunoglobulin superfamily. Preferably, the anti-PD-1 antibody is a recombinant humanized anti-PD-1 monoclonal antibody.

According to one embodiment, the anti-PD-1 antibody comprises the CDRs, the variable heavy chain region, and/or the variable light region of any one of the antibodies disclosed herein.

In certain embodiments, the anti-PD-1 antibody of the invention is a chimeric anti-PD-1 antibody c1G4 and/or humanized anti-PD-1 h1G4, comprising a light chain (LC) variable domain sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14). In some embodiments, the variant comprises at least 1, at least 2, at least 3, at least 4, at least 5, at least 6, at least 7, at least 8, at least 9, or at least 10 amino acid substitutions in one or more of SEQ ID Nos. 9-14.

Full length amino acid and nucleotide sequences of light and heavy chains of c1G4 and h1G4 and their CDRs sequences are provided in the Sequence Listing below.

Also provided by the invention is an anti-PD-1 antibody or antigen binding fragment thereof, comprising a heavy chain sequence comprising the amino acid sequence set forth in (SEQ ID NO:4) and a light chain sequence comprising the amino acid sequence set forth in SEQ ID NO:2).

Also provided by the invention is a humanized anti-PD-1 antibody or antigen binding fragment thereof, comprising the amino acid sequence set forth in (SEQ ID NO:8) and a light chain sequence comprising the amino acid sequence set forth in SEQ ID NO:6).

The invention further provides affinity matured antibodies against humanized h1G4 anti-PD-1 antibody. In certain embodiments, the matured anti-PD-1 antibody (e.g., anti-PD-1 antibody, 33B) of the invention comprises a light chain (LC) variable domain sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain (HC) variable domain sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20).

In other embodiments, the matured anti-PD-1 antibody (e.g., anti-PD-1 antibody, 66E) of the invention comprises a light chain (LC) variable domain sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23).

In certain embodiments, the matured anti-PD-1 antibody (e.g., anti-PD-1 antibody, 711D) of the invention comprises a light chain (LC) variable domain sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain (HC) variable domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

The heavy and light chain variable domains and CDRs are combined in all possible pair-wise combinations to generate a number of anti-PD-1 antibodies.

In certain embodiments, the amino acid substitution(s) are conservative amino acid substitution(s). In certain embodiments, the amino acid substitutions do not substantially reduce the ability of the antibody to bind antigen. For example, conservative alterations (e.g., conservative substitutions as provided herein) that do not substantially reduce PD-1 binding affinity may be made. The binding affinity of anti-PD-1 antibody variants can be assessed using methods described in the Examples below.

Conservative substitutions are shown in Table 3 under the heading of "conservative substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved PD-1 binding, decreased immunogenicity, or improved ADCC or CDC.

TABLE 3

CONSERVATIVE SUBSTITUTIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity.

Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, the anti-PD-1 antibody comprises a light chain variable domain ($V_L$) sequence comprising (1) a CDR-L1 comprising an amino acid sequence selected from the group consisting of SEQ ID Nos: 9, 21 and 24; (2) a CDR-L2 comprising an amino acid sequence of SEQ ID Nos: 10 or 16; (3) a CDR-L3 comprising an amino acid sequence selected from the group consisting of SEQ ID Nos: 11, 17, 22, and a heavy chain variable domain sequence ($V_H$) comprising (1) a CDR-H1 comprising an amino acid sequence of SEQ ID Nos: 12 or 18; (2) a CDR-H2 comprising an amino acid sequence of SEQ ID Nos: 13 or 19; and (3) a CDR-H3 comprising an amino acid sequence selected from the group consisting of SEQ ID Nos: 14, 20, 23, and 25.

The heavy and light chain variable domains are combined in all possible pair-wise combinations to generate a number of anti-PD-1 antibodies.

In certain embodiments, the anti-PD-1 antibody may lack an N-glycosylation motif in the heavy chain or light chain variable region which can cause differences within a batch of antibodies resulting in altered function, immunogenicity, or stability. Methods of analyzing antibody glycosylation include, but are not limited to, e.g., chromatography (such as cation exchange chromatography (CEX) or liquid chromatography), mass spectrometry (such as electrospray ionization mass spectrometry), and capillary electrophoresis-sodium dodecyl sulfate. Such methods are described in, e.g., Jung et al. (2011) Curr Op Biotechnol. 22(6):858-67; Cummings R D, Etzler M E. Antibodies and Lectins in Glycan Analysis. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 45; Mulloy B, Hart G W, Stanley P. Structural Analysis of Glycans. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 47; Leymarie, et al. (2012) Anal Chem. 84(7): 3040-3048; Fernandez (2005) European Biopharmaceutical Review. pp 106-110; and Raju, T. (2013) Methods Mol Biol. 988: 169-180.

In certain embodiments, the anti-PD-1 antibody has a stronger binding affinity for a PD-1 than it has for a homologue of that PD-1. Normally, the anti-PD-1 antibody "binds specifically" to PD-1 (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a member of the PD-1 family which is at least about 50-fold, or at least about 500-fold, or at least about 1000-fold weaker than its binding affinity for PD-1. The anti-PD-1 antibody that binds specifically to PD-1 can be of any of the various types of antibodies as defined above, but preferably is a humanized or human antibody.

In some embodiments, the extent of binding of the anti-PD-1 antibody to a non-target protein is less than about 10% of the binding of the antibody to PD-1 as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$M, alternatively at least about $10^{-5}$M, alternatively at least about $10^{-6}$M, alternatively at least about $10^{-7}$M, alternatively at least about $10^{-8}$M, alternatively at least about $10^{-9}$ M, alternatively at least about $10^{-10}$M, alternatively at least about $10^{-11}$ M, alternatively at least about $10^{-12}$M, or greater. In one embodiment, the term "specific binding" refers to binding where a molecule binds to a particular polypeptide or epitope on a particular polypeptide without substantially binding to any other polypeptide or polypeptide epitope.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., such as an anti-PD-1 antibody described herein). In some embodiments, the anti-PD-1 antibody exhibits similar antibody-dependent cell-mediated cytotoxicity (ADCC) effector function as OPDIVO® or Nivolumab, as demonstrated by, e.g., assays described in the Example.

For example, in certain embodiments, ADCC effector function activity of an anti-PD-1 antibody described herein is at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, or more than 100% (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or about 130%) of the ADCC effector function activity of OPDIVO® (Nivolumab) including any range between these values.

In certain embodiments, the anti-PD-1 antibody exhibits similar binding affinity for PD-1 as OPDIVO®. In certain embodiments, binding to PD-1 is demonstrated by ELISA, as described in the Examples. For example, the binding affinity of the anti-PD-1 for PD-1 is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than 100% higher (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or more than about 125%) than the binding affinity of OPDIVO® (Nivolumab) for PD-1.

In certain embodiments, the anti-PD-1 antibody binds a human PD-1 with a Kd between about 0.1 pM to 200 pM (0.2 nM), e.g., about 0.1 pM, about 0.25 pM, about 0.5 pM, about 0.75 pM, about 1 pM, about 5 pM, about 10p M, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, about 150 pM, about 160 pM, about 170 pM, about 180 pM, about 190 pM, or more than about 190 pM, including any range between these values. In certain embodiments, the binding affinity of the anti-PD-1 antibody to PD-1 is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than about 100% higher (e.g., about 105%, about 110%, about 120%, or about 130%) higher than the binding affinity of OPDIVO® (Nivolumab) to PD-1. In certain embodiments, the binding affinity of the anti-PD-1 to PD-1 is about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.25-fold, about 2.5-fold, about 2.75 fold, about 3-fold, about 3.25-fold, about 3.5-fold, about 3.75-fold, about 4-fold, about 4.25-fold, about 4.5-fold, about 4.75-fold, or more than about 4.75-fold higher than the binding affinity of OPDIVO® (Nivolumab) to PD-1, including any range in between these values.

In certain embodiments, the anti-PD-1 antibodies provided herein have prolonged in vivo half-lives as compared to OPDIVO®. In certain embodiments, the in vivo half-life of an anti-PD-1 antibody described herein is no shorter than the in vivo half-life of OPDIVO®.

In certain embodiments, the anti-PD-1 antibodies provided herein exhibit pharmacokinetic properties that are similar to those of OPDIVO® (Nivolumab) or its biosimilar. In certain embodiments, the anti-PD-1 antibodies provided herein exhibit an AUC (area under curve) that is about 50%, about 55%, about 60%, about 65%, about 70%, about 75%, about 80%, about 85%, about 90%, about 95%, or greater than 95% (such as about 96%, about 97%, about 98%, about 99%, or more than about 99%) of the serum concentration-time profiles of OPDIVO® (Nivolumab) or its biosimilar, including any range between these values.

In certain embodiments, the antibody comprises an Fc sequence of a human IgG, e.g., human IgG1 or human IgG4. In certain embodiments, the Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function. For example, WO 00/42072 and Shields et al. J Biol. Chem. 9(2): 6591-6604 (2001) describes antibody variants with improved or diminished binding to FcRs. The contents of those publications are specifically incorporated herein by reference. The antibody can be in the form of a Fab, Fab', a F(ab)'2, single-chain Fv (scFv), an Fv fragment; a diabody and a linear antibody. Also, the antibody can be a multispecific antibody that binds to PD-1, but also binds one or more other targets and inhibits their function. The antibody can be conjugated to a therapeutic agent (e.g., cytotoxic agent, a radioisotope and a chemotherapeutic agent) or a label for detecting PD-1 in patient samples or in vivo by imaging (e.g., radioisotope, fluorescent dye and enzyme). Other modifications include the conjugation of toxin to anti-PD-1 antibodies provided herein.

Nucleic acid molecules encoding the anti-PD-1 antibodies, expression vectors comprising nucleic acid molecules encoding the CDRs and/or a heavy chain variable domain and/or a light chain variable domain described herein, and cells comprising the nucleic acid molecules are also contemplated. These antibodies can be used in the therapies described herein and to detect PD-1 protein in patient samples (e.g., via FACS, immunohistochemistry (IHC) ELISA assays) or in patients.

Monoclonal Antibodies

Monoclonal antibodies can be prepared, e.g., using hybridoma methods, such as those described by Kohler and Milstein, Nature, 256:495 (1975) or can be made by recombinant DNA methods (U.S. Pat. No. 4,816,567) or can be produced by the methods described herein in the Examples below. In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, New York: Academic Press, 1986, pp. 59-103). Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al. MONOCLONAL ANTIBODY PRODUCTION TECHNIQUES AND APPLICATIONS, Marcel Dekker, Inc.: New York, 1987, pp. 51-63).

The culture medium in which the hybridoma cells are cultured can thenbe assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem. 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies provided herein can be readily isolated and sequenced using conventional procedures (e.g., by using oligonucleotide probes that are capable of binding specifically to genes encoding the heavy and light chains of murine antibodies). The hybridoma cells provided herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a nonimmunoglobulin polypeptide. Such a non-immunoglobulin polypeptide can be substituted for the constant domains of an antibody provided herein, or can be substituted for the variable domains of one antigen-combining site of an antibody provided herein to create a chimeric bivalent antibody.

In certain embodiments, an anti-PD-1 antibody provided by the invention is expressed by a stable mammalian cell line. In certain embodiments, an anti-PD-1 antibody provided by the invention is expressed from a stable mammalian cell line at a titer of about 2.0 grams/liter, about 2.5 grams/liter, about 3.0 grams/liter, about 3.5 grams/liter, about 4.0 grams/liter, about 4.5 grams/liter, about 5.0 grams/liter, about 5.5 grams/liter, about 6 grams/liter, about 6.5 grams/liter, about 7.0 grams/liter, or more than about 7.0 grams/liter, including any range in between these values. In certain embodiments, the stable mammalian cell line from which an anti-PD-1 antibody provided by the invention is expressed is a CHO cell line.

In certain embodiments, the antibodies are monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

Human and Humanized Antibodies

The antibodies can be humanized antibodies or human antibodies. Humanized forms of non-human (e.g., murine)

antibodies are chimeric immunoglobulins, immunoglobulin chains, or fragments thereof (such as Fv, Fab, Fab', F(ab')$_2$, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al. Nature, 321: 522-525 (1986); Riechmann et al., Nature, 332: 323-329 (1988); Presta, Curr. Op. Struct. Biol., 2:593-596 (1992).

Generally, a humanized antibody has one or more amino acid residues introduced into it from a source that is non-human. These non-human amino acid residues are often referred to as "import" residues, which are typically taken from an "import" variable domain. According to one embodiment, humanization can be essentially performed following the method of Winter and co-workers (Jones et al. Nature, 321: 522-525 (1986); Riechmann et al. Nature, 332: 323-327 (1988); Verhoeyen et al. Science, 239: 1534-1536 (1988)), by substituting rodent CDRs or CDR sequences for the corresponding sequences of a human antibody. Accordingly, such "humanized" antibodies are antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al. PNAS USA, 90:2551 (1993); Jakobovits et al., Nature, 362:255-258 (1993); Bruggemann et al. in Immunol. 7:33 (1993); U.S. Pat. Nos. 5,545,806, 5,569,825, 5,591,669; 5,545,807; and WO 97/17852.

Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., Bio/Technology, 10:779-783 (1992); Lonberg et al., Nature, 368: 856-859 (1994); Morrison, Nature, 368: 812-813 (1994); Fishwild et al. Nature Biotechnology, 14: 845-851 (1996); Neuberger, Nature Biotechnology, 14: 826 (1996); Lonberg and Huszar, Intern. Rev. Immunol., 13: 65-93 (1995).

Alternatively, phage display technology (McCafferty et al., Nature 348:552-553, 1990) can be used to produce human antibodies and antibody fragments in vitro, from immunoglobulin variable (V) domain gene repertoires from unimmunized donors. According to one embodiment of this technique, antibody V domain sequences are cloned in frame into either a major or minor coat protein gene of a filamentous bacteriophage, such as M13 or fd, and displayed as functional antibody fragments on the surface of the phage particle. Phage display can be performed in a variety of formats, e.g., as described below in the Examples section or as reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human antibodies can also be produced using various techniques known in the art, including phage display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985) and Boerner et al., J. Immunol., 147(1): 86-95 (1991).

Multispecific Antibodies

Multispecific antibodies are monoclonal, preferably human or humanized, antibodies that have binding specificities for two or more different antigens (e.g., bispecific antibodies have binding specificities for at least two antigens). For example, one of the binding specificities can be for the a5~1 protein, the other one can be for any other antigen. According to one preferred embodiment, the other antigen is a cell-surface protein or receptor or receptor subunit. For example, the cell-surface protein can be a natural killer (NK) cell receptor. Thus, according to one embodiment, a bispecific antibody of this invention can bind both PD-1 and, e.g., a second cell surface receptor.

Suitable methods for making bispecific antibodies are well known in the art. For example, the recombinant production of bispecific antibodies is based on the co-expression of two immunoglobulin heavy-chain/light-chain pairs, where the two heavy chains have different specificities. Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., EMBO, 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., Methods in Enzymology, 121: 210 (1986).

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., PNAS USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron et al., J. Exp. Med., 176: 1191-1195 (1992) and Shapes, J. Immunol., 148: 2918-2922 (1992). Homodimeric antibodies with enhanced anti-tumor activity can also be prepared using heterobifunctional cross-linkers as described in Wolff et al., Cancer Research, 53: 2560-2565 (1993). Alternatively, an antibody can be engineered that has dual Fc regions and can thereby have enhanced complement lysis and ADCC capabilities. See, Stevenson et al., Anti-Cancer Drug Design 3: 219-230 (1989).

Mutations or alterations in the Fc region sequences can be made to improve FcR binding (e.g., FcγR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields, R L et al. (2001) JBC 276(6)6591-6604; Presta, L. G., (2002) Biochemical Society Transactions 30(4):487-490; and WO 00/42072.

According to one embodiment, the Fc receptor mutation is a substitution at least one position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is according to the EU numbering system. In some embodiments, the Fc receptor mutation is a D265A substitution. In some embodiments, the Fc receptor mutation is a N297 A substitution. Additional suitable mutations are set forth in U.S. Pat. No. 7,332,581.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include *diphtheria* A chain, nonbinding active fragments of *diphtheria* toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y and $^{186}$Re. Exemplary chemotherapeutic agents useful in the generation of such immunoconjugates include those described elsewhere herein.

In certain embodiments, an anti-PD-1 antibody provided herein is conjugated to maytansine, a maytansinoid, or calicheamicin. In certain embodiments, an anti-PD-1 antibody provided herein is conjugated to the maytansinoid DM1.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Covalent Modifications

Covalent modifications of the anti-PD-1 antibodies and fragments thereof are included within the scope of this invention. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the polypeptide comprises linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Chimeric Molecules

An anti-PD-1 antibody, and/or fragment thereof, of the present invention can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 (Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)]; and the Herpes Simplex virus glycoprotein D (gD) tag and its antibody (Paborsky et al., Protein Engineering, 3(6):547-553 (1990)]. Other tag polypeptides include the Flag-peptide (Hopp et al., BioTechnology, 6:1204-1210 (1988)]; the KT3 epitope peptide (Martin et al., Science, 255:192-194 (1992)]; an α-tubulin epitope peptide (Skinner et al., J. Biol. Chem., 266:15163-15166 (1991)]; and the T7 gene 10 protein peptide tag (Lutz-Freyermuth et al., Proc. Natl. Acad. Sci. USA, 87:6393-6397 (1990)).

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this invention include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

Immunoliposomes

The antibodies disclosed herein can also be formulated as immunoliposomes. Liposomes containing the antibody are prepared by methods known in the art, such as described in Epstein et al., PNAS USA, 82: 3688 (1985); Hwang et al., PNAS USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction. An anti-neoplastic agent, a growth inhibitory agent, or a chemotherapeutic agent (such as doxorubicin) is optionally also contained within the liposome. See, Gabizon et al., J. National Cancer Inst., 81(19): 1484 (1989).

Treatment Using Anti-PD-1 Antibodies

The anti-PD-1 antibodies and/or fragments thereof, and/or compositions provided herein can be administered to subjects (e.g., mammals such as humans) to treat diseases and disorders involving abnormal PD-1 activity, including, for example, cancer (such as head and neck cancer, throat cancer, colorectal cancer, lung cancer, etc.). In certain embodiments, the invention provides anti-PD-1 antibodies described herein (or fragments thereof) for use in the manufacture of a medicament for the treatment of cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject. In certain embodiments, the invention provides anti-PD-1 antibodies described herein (or fragments thereof) for use in treating cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject.

In certain embodiments, the invention provides pharmaceutical compositions comprising an anti-PD-1 antibody provided herein (or fragments thereof) for use in treating cancer (melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) or be diagnosed with a cancer or any other disease having abnormal PD-1 expression or activity.

Many diagnostic methods for cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) or any other disease exhibiting abnormal PD-1 activity and the clinical delineation of those diseases are known in the art. Such methods include, but are not limited to, e.g., immunohistochemistry, PCR, fluorescent in situ hybridization (FISH). Additional details regarding diagnostic methods for abnormal PD-1 activity or expression are described in, e.g., Gupta et al. (2009) Mod Pathol. 22(1): 128-133; Lopez-Rios et al. (2013) J Clin Pathol. 66(5): 381-385; Ellison et al. (2013) J Clin Pathol 66(2): 79-89; and Guha et al. (2013) PLoS ONE 8(6): e67782.

Administration can be by any suitable route including, e.g., intravenous, intramuscular, or subcutaneous. In some embodiments, the anti-PD-1 antibodies (or fragments thereof) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving abnormal PD-1 activity. Such agents include, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4, infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, the anti-PD-1 antibodies (or fragments thereof) are conjugated to the additional agent.

In certain embodiments, the anti-PD-1 antibodies (or fragments thereof) and/or compositions provided herein are administered in combination with one or more additional therapies, such as radiation therapy, surgery, chemotherapy, and/or targeted therapy. In certain embodiments, the anti-PD-1 antibodies (or fragments thereof) and/or compositions provided herein are administered in combination with radiation therapy. In certain embodiments, the combination of an anti-PD-1 antibody (or fragment thereof) and/or composition provided herein and radiation therapy is used for treating a cancer selected from the group consisting of melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, and thyroid cancer.

Depending on the indication to be treated and factors relevant to the dosing that a physician of skill in the field would be familiar with, the anti-PD-1 antibodies or fragments thereof, provided herein will be administered at a dosage that is efficacious for the treatment of that indication while minimizing toxicity and side effects. For the treatment of a cancer (such as melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer), a typical dose can be, for example, in the rage of 0.001 to 1000 µg; however, doses below or above this exemplary range are within the scope of the invention. The daily dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values, including any range between the foregoing values). As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising the anti-PD-1 antibody or a fragment thereof can be administered one, two, three, or four times daily. The compositions can also be administered less frequently than daily, for example, six times a week, five times a week, four times a week, three times a week, twice a week, once a week, once every two weeks, once every three weeks, once every month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection.

The antibody (or a fragment thereof) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once every month, once every two months, once every three months, or once every six months. The antibody (or a fragment thereof) may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C \times 100)$, where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%, about 94%, about 95%, or more than 95%. In certain embodiments the % TGI of an anti-PD-1 is the same as or greater than the % TGI of OPDIVO®, such as about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, including any range in between these values, or more than about 2.7-fold greater than the % TGI of OPDIVO®.

Pharmaceutical Formulations

The anti-PD-1 antibodies (or fragments thereof) can be formulated with suitable carriers or excipients so that they are suitable for administration. Suitable formulations of the antibodies are obtained by mixing an antibody (or fragment thereof) having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent. Such molecules are suitably present in combination in amounts that are effective for the purpose intended. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Sustained-release preparations may be prepared. Suitable examples of sustained release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Lipofectins or liposomes can be used to deliver the polypeptides and antibodies (or fragments thereof) or compositions of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., PNAS USA, 90: 7889-7893 (1993).

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In certain embodiments, the formulation comprises an anti-PD-1 antibody described herein at a concentration of greater than about 0.5 mg/ml, greater than about 1 mg/ml, greater than about 2 mg/ml, greater than about 3 mg/ml, greater than about 4 mg/ml, greater than about 5 mg/ml, greater than about 6 mg/ml, greater than about 7 mg/ml, greater than about 8 mg/ml, greater than about 9 mg/ml, greater than about 10 mg/ml, greater than about 11 mg/ml, greater than about 12 mg/ml, greater than about 13 mg/ml, greater than about 14 mg/ml, greater than about 15 mg/ml, greater than about 16 mg/ml, greater than about 17 mg/ml, greater than about 18 mg/ml, greater than about 19 mg/ml, greater than about 20 mg/ml, greater than about 21 mg/ml, greater than about 22 mg/ml, greater than about 23 mg/ml, greater than about 24 mg/ml, greater than about 25 mg/ml, greater than about 26 mg/ml, greater than about 27 mg/ml, greater than about 28 mg/ml, greater than about 29 mg/ml, or greater than about 30 mg/ml, including any range in between these values.

In certain embodiments, the anti-PD-1 antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about-25 mg/ml, including any range in between these values) in a buffer comprising a citrate, NaCl, acetate, succinate, glycine, polysorbate 80 (Tween 80), or any combination of the foregoing. In certain embodiments, the anti-PD-1 antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 100 mM to about 150 mM glycine. In certain embodiments, the anti-PD-1 antibody is formulated in a buffer comprising about 50 mM to about 100 mM NaCl. In certain embodiments, the anti-PD-1 antibody is formulated (e.g., at a concentration greater than about mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 10 mM to about 50 mM acetate. In certain embodiments, the anti-PD-1 antibody is formulated in a buffer comprising about 10 mM to about 50 mM succinate. In certain embodiments, the anti-PD-1 antibody is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 0.005% to about 0.02% polysorbate 80. In certain embodiments, the anti-PD-1 antibody is formulated in a buffer having a pH between about 5.1 and 5.6. In certain embodiments, the anti-PD-1 antibody is formulated in a buffer comprising 10 mM citrate, 100 mM NaCl, 100 mM glycine, and 0.01% polysorbate 80, wherein the formulation is at pH=5.5.

In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an PD-1 antibody described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg·ml, including any range in between these values) is stable at room temperature (such as at about 20-25° C. for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values. In certain embodiments, a formulation (such as a formulation comprising buffer comprising 10 mM citrate, 100 mM NaCl, 100 mM glycine, and 0.01% polysorbate 80, wherein the formulation is at pH=5.5) comprising a PD-1 antibody described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg·ml, including any range in between these values) is stable under accelerated conditions (such as storage at about 37° C.) for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values.

Size exclusion chromatography (SEC) is a well-known and widely used method used in protein stability studies to detect potential fragmentation and aggregation, corresponding to physical and chemical instabilities. In certain embodiments, a formulation comprising 5 mg/ml, 10 mg/ml, 15 mg/ml, 20 mg/ml, or 25 mg/ml of an anti-PD-1 antibody described herein shows less than about a 1.6%, 1.4%, 1.2%, 1.0%, 0.8%, 0.6%, 0.4%, 0.2%, or 0.1% increase in high molecular weight species (HMWS) after 1 week at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-1 antibody described herein shows less than about a 2.0%, 1.8% 1.6%, 1.4%, 1.2%, 1.0%, 0.8%, 0.6%, 0.4%, 0.2%, or 0.1% increase in high molecular weight species after 2 weeks at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-EFGR antibody described herein shows less than about a 3.3%, 3.2%, 3.1%, 3.0%, 2.9%, 2.8%, 2.7%, 2.6%, 2.5%, 2.4%, 2.2%, 2.0%, 1.8%, 1.6%, 1.4%, 1.2%, 1.0%, 0.8%, 0.6%, 0.4%, 0.2%, or 0.1% increase in high molecular weight species after 4 weeks at 37° C., relative to the initial % high molecular weight species, as measured using SEC, including any range in between these values.

In certain embodiments, a formulation comprising 5 mg/ml, 10 mg/ml, 15 mg/ml, 20 mg/ml, or 25 mg/ml of an anti-PD-1 antibody described herein shows less than about a 1.6%, 1.4%, 1.2%, 1.0%, 0.8%, 0.6%, 0.4%, 0.2%, or 0.1% increase in low molecular weight species (LMWS) after 1 week at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-1 antibody described herein shows less than about a 2.0%, 1.8% 1.6%, 1.4%, 1.2%, 1.0%, 0.8%, %, 0.4%, 0.2%, or 0.1% increase in low molecular weight species after 2 weeks at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-1 antibody described herein shows less than about a 2.4%, 2.2%, 2.0%, 1.8% 1.6%, 1.4%, 1.2%, 1.0%, 0.8%, 0.6%, 0.4%, 0.2%, or 0.1% increase in low molecular weight species after 4 weeks at 37° C., relative to the initial % low molecular weight species, as measured using SEC, including any range in between these values.

In certain embodiments, a formulation comprising 5 mg/ml, 10 mg/ml, 15 mg/ml, 20 mg/ml, or 25 mg/ml of an anti-PD-1 antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 1 week at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-PD-1 antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-PD-1 antibody described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values.

Cation exchange chromatography (CEX) is a well-known and widely used tool to detect protein degradation events such as deamidation or oxidation (Moorhouse et al. (1997) J. Pharm. Biomed. Anal. 16, 593-603). Degradation products are typically referred to as acidic or basic species. Acidic species are the variants that elute earlier than the main peak from CEX, while basic species are the variants that elute later than the main peak from CEX. In certain embodiments, the acidic peak fraction of a formulation comprising 5 mg/ml, 10 mg/ml, 15 mg/ml, 20 mg/ml, or 25 mg/ml of an anti-PD-1 antibody described herein is no more than about 1.7%, 8%, 9%, 10%, 11%, 12%, 13%, 14%, or 15% of total protein after 1 week at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-PD-1 antibody described herein is no more than about 8%, 9%, 10%, 11%, 12%, 13%, 14%, 15%, 16%, 17%, or 18% of total protein after 2 weeks at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-PD-1 antibody described herein is no more than about 8%, 9%, 10%, 11%, 12%, 13%, 14%, 15%, 16%, 17%, 18%, 19%, 20%, 21%, 22%, 23%, 24%, 25%, 26%, or 27% of total protein after 2 weeks at 37° C., as measured using CEX, including any range in between these values.

In certain embodiments, the basic peak fraction of a formulation comprising 5 mg/ml, 10 mg/ml, 15 mg/ml, 20 mg/ml, or 25 mg/ml of an anti-PD-1 antibody described herein is no more than about 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-1 antibody described herein is no more than about 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-1 antibody described herein is no more than about 39%, 40%, 41%, 42%, 43%, 44%, 45%, or 46% of total protein after 4 weeks at 37° C., as measured using CEX, including any range in between these values. In certain embodiments, the main peak fraction of a formulation comprising 5 mg/ml, 10 mg/ml, 15 mg/ml, 20 mg/ml, or 25 mg/ml of an anti-PD-1 antibody described herein is no less than about 32%, 33%, 34%, 35%, 36%, 37%, 38%, 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-1 antibody described herein is no less than about 32%, 33%, 34%, 35%, 36%, 37%, 38%, 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-1 antibody described herein is no less than about 32%, 33%, 34%, 35%, 36%, 37%, 38%, 39%, 40%, 41%, 42%, 43%, 44%, 45%, or 46% of total protein after 4 weeks at 37° C., as measured using CEX, including any range in between these values.

The formulations to be used for in vivo administration must be sterile. This is readily accomplished by, e.g., filtration through sterile filtration membranes.

Methods of Diagnosis and Imaging Using Anti-PD-1 Antibodies

Labeled anti-PD-1 antibodies, fragments thereof, and derivatives and analogs thereof, which specifically bind to a PD-1 polypeptide can be used for diagnostic purposes to detect, diagnose, or monitor diseases and/or disorders associated with the expression, aberrant expression and/or activity of PD-1. For example, the anti-PD-1 antibodies (or fragments thereof) provided herein can be used in in situ, in vivo, ex vivo, and in vitro diagnostic assays or imaging assays. Methods for detecting expression of a PD-1 polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression.

Additional embodiments provided herein include methods of diagnosing a disease or disorder associated with expression or aberrant expression of PD-1 in an animal (e.g., a mammal such as a human). The methods comprise detecting PD-1 molecules in the mammal. In certain embodiments, diagnosis comprises: (a) administering an effective amount of a labeled anti-PD-1 antibody (or fragment thereof) to a mammal (b) waiting for a time interval following the administering for permitting the labeled anti-PD-1 antibody (or fragment thereof) to preferentially concentrate at sites in the subject where the PD-1 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of PD-1. Background level can be determined by various methods including, comparing the amount of labeled molecule detected to a standard value previously determined for a particular system.

Anti-PD-1 antibodies (or fragments thereof) provided herein can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium $^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

Alternatively, or additionally, one can measure levels of a PD-1 polypeptide-encoding nucleic acid or mRNA in the cell, e.g., via fluorescent in situ hybridization using a nucleic acid based probe corresponding to a PD-1 encoding nucleic acid or the complement thereof; (FISH; see W098/454 79 published October 1998), Southern blotting, Northern blotting, or polymerase chain reaction (PCR) techniques, such as real time quantitative PCR (RT-PCR). One can also study PD-1 overexpression by measuring shed antigen in a biological fluid such as serum, e.g., using antibody-based assays (see also, e.g., U.S. Pat. No. 4,933,294 issued Jun. 12, 1990; W091/05264 published Apr. 18, 1991; U.S. Pat. No. 5,401,638 issued Mar. 28, 1995; and Sias et al., J. Immunol.

Methods 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the cells can be evaluated, e.g., by external scanning for radioactivity or by analyzing a sample (e.g., a biopsy or other biological sample) taken from a mammal previously exposed to the antibody.

Articles of Manufacture and Kits

Another embodiment provided herein is an article of manufacture containing materials useful for the treatment of cancer, such as melanoma, NSCLC, head and neck, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer, and salivary cancer. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is an anti-PD-1 antibody (or fragment thereof) provided herein. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating cancer (such as head and neck cancer, lung cancer, or colorectal cancer).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of PD-1 in patients, optionally in combination with the articles of manufacture. For isolation and purification of PD-1, the kit can contain an anti-PD-1 antibody (or fragment thereof) provided herein coupled to beads (e.g., SEPHAROSE™ beads). Kits can be provided which contain the antibodies (or fragments thereof) for detection and quantitation of PD-1 in vitro, e.g. in an ELISA or a Western blot. As with the article of manufacture, the kit comprises a container and a label or package insert on or associated with the container. For example, the container holds a composition comprising at least one anti-PD-1 antibody provided herein. Additional containers may be included that contain, e.g., diluents and buffers, control antibodies. The label or package insert may provide a description of the composition as well as instructions for the intended in vitro or diagnosticuse.

LIST OF EMBODIMENTS

Embodiments provided by the invention include, but are not limited to those listed herein below.

Embodiment 1: An anti-PD-1 antibody or an antigen binding fragment thereof comprising a light chain variable domain ($V_L$) sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14).

Embodiment 2: An anti-PD-1 antibody or an antigen binding fragment thereof comprising a light chain variable domain ($V_L$) sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain variable domain ($V_H$) sequence comprising: (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20).

Embodiment 3: An anti-PD-1 antibody or an antigen binding fragment thereof comprising a light chain variable domain ($V_L$) sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain variable ($V_H$) domain sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23).

Embodiment 4: An anti-PD-1 antibody or an antigen binding fragment thereof comprising a light chain variable domain ($V_L$) sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

Embodiment 5: The antigen binding fragment of the anti-PD-1 antibody according to any one of embodiments 1-4, wherein the antigen binding fragment is selected from the group consisting of a Fab, Fab', a F(ab)'2, a single-chain Fv (scFv), an Fv fragment, a diabody, and a linear antibody.

Embodiment 6: The anti-PD-1 antibody or an antigen binding fragment thereof according to any one of embodiments 1-5, wherein the antibody is a multispecific antibody.

Embodiment 7: The anti-PD-1 antibody or antigen binding fragment thereof according to any one of embodiments 1-6 conjugated to a therapeutic agent.

Embodiment 8: The anti-PD-1 antibody or antigen binding fragment thereof according to any one of embodiments 1-7 conjugated to a label.

Embodiment 9: The anti-PD-1 antibody or an antigen binding fragment thereof according to embodiment 8, wherein the label is selected from the group consisting of a radioisotope, a fluorescent dye, and an enzyme.

Embodiment 10: An isolated nucleic acid molecule that encodes the anti-PD-1 antibody or antigen binding fragment thereof according to any one of embodiments 1-4.

Embodiment 11: An expression vector encoding the nucleic acid molecule of embodiment 10.

Embodiment 12: A cell comprising the expression vector of embodiment 11.

Embodiment 13: A method of producing an anti-PD-1 antibody or an antigen binding fragment thereof comprising culturing the cell of embodiment 12 and recovering the antibody from the cell culture.

Embodiment 14: A composition comprising the anti-PD-1 antibody or an antigen binding fragment thereof according to any one of embodiments 1-9 and a pharmaceutically acceptable carrier.

Embodiment 15: A method of detecting a PD-1 protein in sample from a patient by contacting the anti-PD-1 antibody or an antigen binding fragment thereof according to any one of embodiments 1-9 to the sample and detecting the anti-PD-1 antibody bound to the PD-1 protein.

Embodiment 16: The method according to embodiment 15, wherein the anti-PD-1 antibody or an antigen binding fragment thereof is used an immunohistochemistry assay (IHC) or in an ELISA assay.

Embodiment 17: A method of treating cancer in a subject, comprising administering an effective amount of the composition of embodiment 14 to the subject.

Embodiment 18: The method of embodiment 17, wherein the cancer is selected from the group consisting of melanoma, NSCLC, head and neck, urothelial cancer, triple-negative breast cancer (TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer, esophageal cancer, nasopharyngeal carcinoma (NPC), biliary tract cancer, colorectal cancer, breast cancer, cervical cancer, thyroid cancer, and salivary cancer.

Embodiment 19: The method of embodiments 17 and 18, wherein the subject is further administered a therapeutic agent selected from the group consisting of an anti-neoplastic agent, a chemotherapeutic agent, a growth inhibitory agent and a cytotoxic agent.

Embodiment 20: The method of embodiment 19, wherein the subject is further treated with a radiation therapy and/or surgery.

Embodiment 21: The method of embodiments 17 and/or 18, wherein the subject is further administered one or more therapeutic antibody against VEGF, VEGFR2, or EGFR.

EXAMPLES

Example 1

Development of Anti-PD1 Antibodies

The development of anti-PD-1 antibodies is summarized as follows. Positive anti-PD-1 antibody clones were identified by screening of a Fab phage library generated from hybridomas constructed from PD-1 (purified recombinant 6×His-tagged PD-1_ECD antigen antigen ("6×His" disclosed as SEQ ID NO: 26)) immunized mice. In vitro functional assays, described in further detail below, were performed to characterize the clones.

Briefly, serial dilutions of hybridoma clones were incubated with PD1-His protein coated plates for one hour at room temperature, and PD1 binding activity was monitored at 450 nm. The plates were blocked with 5% milk in phosphate buffered saline (PBS) for 1 hour at room temperature and washed with PBS-tween 20 (PBST) prior to addition of hybridoma dilutions.

After incubation with hybridoma clones, the plates were washed with PBST, incubated with 1:4000 anti-mouse IGG-HRP at room temperature for 1 hour, washed with PBST, developed with tetramethylbenzidine (TMB), and finally H2504 was used for stopping the reaction, and absorbance at 450 nm was measured.

Flow cytometry showed that clone ID numbers 11, 12, 14, 16, 18, 20, 24, 27, and 28 could bind PD-1. The flow cytometry conditions for assessing PD-1 binding include the steps of: 1) 4E+05 PD-1 expressed CHO-S cells were washed with PBS (2% FBS) twice; 2) Added hybridoma supernatant, incubated at 4° C. for 30 min; 3) Centrifuged cells for 5 min at 500×g; 4) Washed with PBS (2% FBS) twice; 5) Added 1:150 diluted goat anti-human IgG-FITC 30 min incubation at 4° C.; 6) Washed cells with PBS (2% FBS) twice; and 7) Suspended cells in 50 µl 1×PBS, analysis by flow cytometry.

Flow cytometry was used to assess the ability of the hybridoma supernatants to block the binding between PD-L1 and PD1. The results revealed that clone #11 blocked binding equivalent to the referenced anti-PD-1 antibody, e.g., Nivolumab. The flow cytometry binding assay conducted includes the steps of: 1) 4E+05 cells per sample washed with PBS (2% FBS) twice; 2) Mixed 8 ug/mL of Biotin-PDL1 and hybridoma supernatant, the volume ratio was 1:1; 3) Added the 60 uL of mixture from step 2 to cells and incubated for 30 min at 4° C.; 4) Washed cell twice with PBS (2% FBS); 5) Incubated cell with avidin-FITC (1:65 dilution) for 30 min at 4° C.; and 6) Washed cell twice with PBS (2% FBS).

One positive PD-1 colony (c1G4) was identified in SS320 competent cells. Characteristics and sequences of c1 G4 clone are provided below.

Example 2

Generating the Humanized Anti-PD-1 Antibody 1G4 (h1G4)

The humanized anti-PD-1 antibody 1G4 (h1G4) was generated using human germline light chain variable region IGKV1-39*01 and human germline heavy chain variable region IGHV3-11*04. Briefly, humanization was done by grafting the CDR residues from the light chain and heavy chain of chimericc1G4 to a similar light chain and heavy chain frameworks of human immunoglobulin. Libraries of the CDRs-grafted humanized antibody can be generated for further in vitro phage display-based affinity maturation to enhance the affinity to its antigen. Sequence alignment for c1G4 and h1G4 is shown in FIGS. 8A and 8B. FIG. 8A shows an amino acid sequence alignment of the light chains of chimeric c1G4, humanized h1G4, human germline light chain variable region IGKV1-39*01, and Nivolumab (NIV). FIG. 8B shows an amino acid sequence alignment of the heavy chains of chimeric c1G4, humanized h1G4, human germline heavy chain variable region IGHV3-11*04, and Nivolumab (NIV). The CDRs (Complementary Determining Regions) grafted from c1G4 for humanization were marked in bold and underlined text.

Example 3

Determination of Equilibrium Dissociation Constant (KD) of c1G4 and h1G4

The binding affinity and kinetics were measured using surface plasmon resonance (SPR). Anti-human IgG Fc was first immobilized on a sensor chip and then capture the referenced anti-PD-1 antibody, c1G4, and h1G4 with a Rmax~150 RU. Experiments were carried out at 25° C., and measurements were made with serial dilutions of PD-1-His from 58.8 nM to 7.35 nM passing over the captured antibodies in HBS-P+ buffer supplemented with 0.1% (w/v) BSA. All data were analyzed with the evaluation software and curves were fit with a 1:1 Langmuir binding model.

Association and dissociation kinetics, along with calculated affinity (KD) were measured by surface plasmon resonance (SPR). Improvement of affinity for c1G4 and h1G4 in contrast to anti-PD-1 ref was also shown in the following Table 4. Data are representative of two independent experiments performed in duplicate.

TABLE 4

| Average (n = 2) | ka [1/(M · s)] | kd [1/s] | KD [M] | Improvement |
|---|---|---|---|---|
| anti-PD-1 ref | 5.86E+05 | 7.43E−04 | 1.77E−09 | 1.00 |
| c1G4 | 2.44E+05 | 1.04E−04 | 4.34E−10 | 4.07 |
| h1G4 | 3.10E+05 | 7.98E−05 | 2.65E−10 | 6.66 |

Example 4

Binding Characteristics of Chimeric c1G4 and Humanized h1G4 Antibodies

Binding of c1G4 to PD-1 Recombinant Protein

ELISA assays were performed to assess the binding of chimeric c1G4 and the referenced anti-PD-1 antibody to PD-1. Serial dilutions of chimeric c1G4 and the referenced anti-PD-1 were captured with PD-1-His in wells of a microtiter dish. The amount of captured antibody in each well was quantified using an anti-human IgG Fc-HRP-conjugated secondary antibody. The HRP-conjugated secondary antibody was added to the wells, and, following an incubation, excess secondary antibody was washed away. TMB was added to the wells, and following incubation, the reaction was stopped, and HRP activity was measured by monitoring the increase in absorbance at 450 nm. The results of ELISAs performed to compare the binding of anti-PD-1 antibodies chimeric c1G4 and the referenced anti-PD-1 antibody to PD-1-His are shown in FIG. 1A.

Figure 1B:
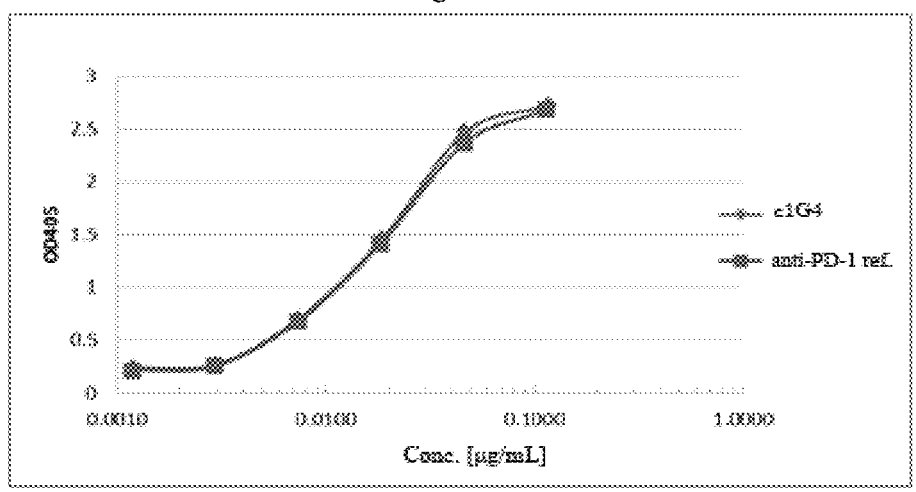

FIG. 1B shows the results of a second set of ELISAs performed to compare the binding of anti-PD-1 antibodies chimeric c1G4 and the referenced anti-PD-1 antibody to PD-1-AP. Serial dilutions of chimeric c1G4 and the referenced anti-PD-1 antibody were captured with anti-human IgG Fc antibody in wells of a microtiter dish. The amount of captured antibody in each well was quantified using AP-conjugated PD-1. Following an incubation, excess PD-1-AP was washed away. Alkaline phosphatase substrate was added to the wells, and following incubation, the reaction was stopped, and AP activity was measured by monitoring the increase in absorbance at 405 nm.

The results indicate that chimeric c1G4 and the referenced anti-PD-1 antibody are able to bind to both PD-1-His and PD-1-AP.

Blocking and Competition of Binding to PD-1 Ligand of c1G4

Figure 2A:
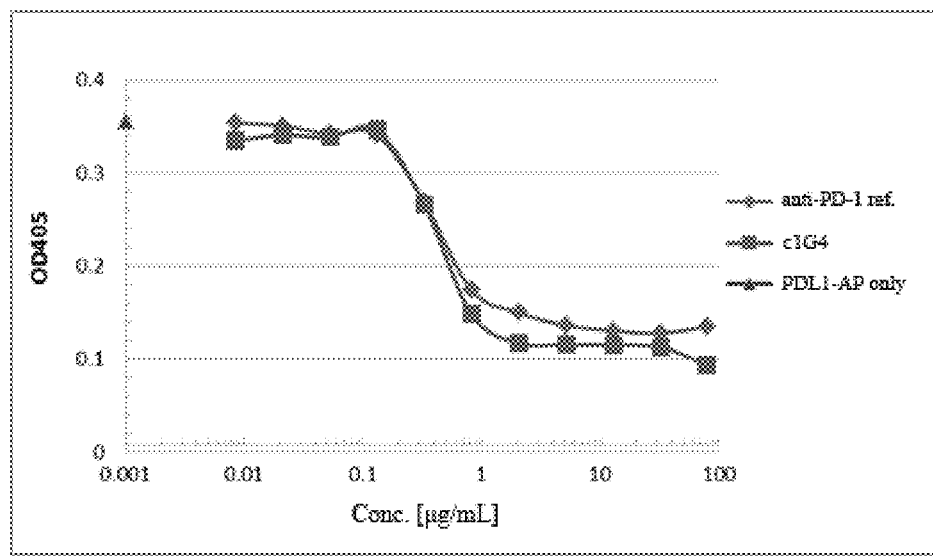
FIGS. 2A-2B. Blocking and competition of binding to PD-1 ligand of c1G4.

Serial dilutions of chimeric c1G4 and the referenced anti-PD-1 antibody were incubated with PD-L1-AP at RT for 2 hours. Each antibody:antigen mixture was added to PD-1-His-coated wells of a microtiter dish. Following an incubation and wash, pNPP was added to the wells and incubated for 1 hour for the detection of bound PD-L1-AP. AP activity was measured by monitoring the increase in absorbance at 405 nm. FIG. 2A shows the results of ELISAs performed to compare the ability of anti-PD-1 antibodies chimeric c1G4 and the referenced anti-PD-1 antibody to block binding of PD-L1 and PD-1. Both chimeric c1G4 and the referenced anti-PD-1 antibody were found to block the binding of PD-L1 to PD-1.

Figure 2B:
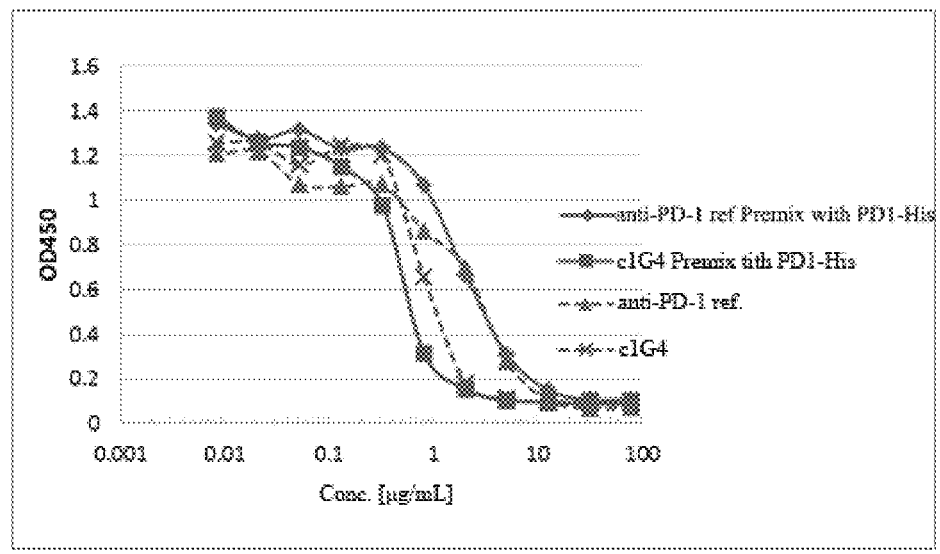

FIG. 2B shows the results of ELISAs performed to determine the ability of anti-PD-1 antibody chimeric c1G4 to compete with the referenced anti-PD-1 antibody for binding to PD-1-His. Serial dilutions of chimeric c1G4 and the referenced anti-PD-1 antibody were pre-mixed with a fixed concentration of PD-1-His (0.1 µg/ml) at room temperature for 2 hours and then bound to a fixed concentration of the referenced anti-PD-1 (4 µg/ml) coated plate. The amount of bound PD-1-His in each well was quantified using an anti-His-HRP-conjugated secondary antibody. Following an incubation, excess secondary antibody was washed away. TMB was added to the wells, and following incubation, the reaction was stopped, and HRP activity was measured by monitoring the increase in absorbance at 450 nm. Fixed concentration of PD-1-His (0.1 µg/ml) was added to fixed concentration of NIV (4 µg/ml) coated plate and incubate at room temperature for 1 hour, and serial dilutions of chimeric c1G4 and the referenced anti-PD-1 antibody were then added to the wells. Following an incubation and wash, the amount of bound PD-1-His in each well was quantified using an anti-His-HRP-conjugated secondary antibody.

These data indicate that both chimeric c1G4 and the referenced anti-PD-1 antibody are able to block the binding of PD-L1 to PD-1, and chimeric c1G4 is able to compete with anti-PD-1 ref for binding to PD-1-His.

Binding of c1G4 and h1G4 to PD-1 Expressing CHO-S Cells

Chinese hamster ovary (CHO) cell lines that express recombinant human PD-1 at the cell surface were developed and used to determine the specificity of PD-1 human monoclonal antibodies by flow cytometry. CHO cells were transfected with expression plasmids containing full length cDNA encoding transmembrane forms of PD-1. Binding of the c1G4 and h1G4 anti-PD-1 monoclonal antibodies was assessed by incubating the transfected cells with the serial-diluted anti-PD-1 monoclonal antibodies in FACS buffer (PBS with 1% FBS). The cells were washed with flow buffer and binding was detected with a biotin-labeled rabbit anti-human IgG Fcγ Ab and streptavidin-PE. Flow cytometric analyses were performed using the Cytomics FC 500 (Beckman Coulter Inc.).

Figure 3A:
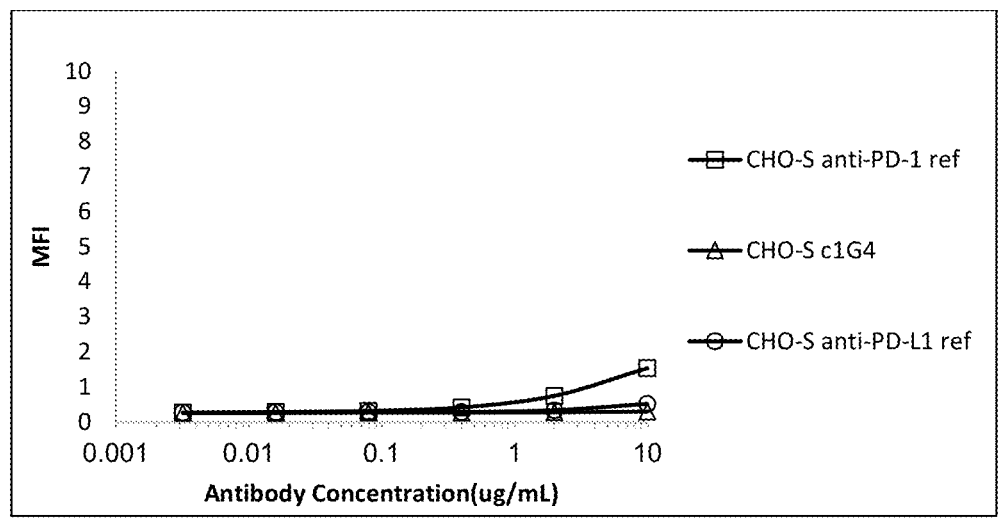
FIGS. 3A-3B. Binding of c1G4 to PD-1 expressing CHO-S cells. The binding of c1G4 antibody to CHO-S cells (FIG. 3A) and PD-1 transfected CHO-S cells (FIG. 3B) were tested by flow cytometry. The referenced anti-PD-1 and anti-PD-L1 antibodies were used as the positive control and negative control, respectively. The data indicate that c1G4 bound to the CHO cells transfected with human PD-1 but not to the non-transfected CHO cells.
Figure 3B:
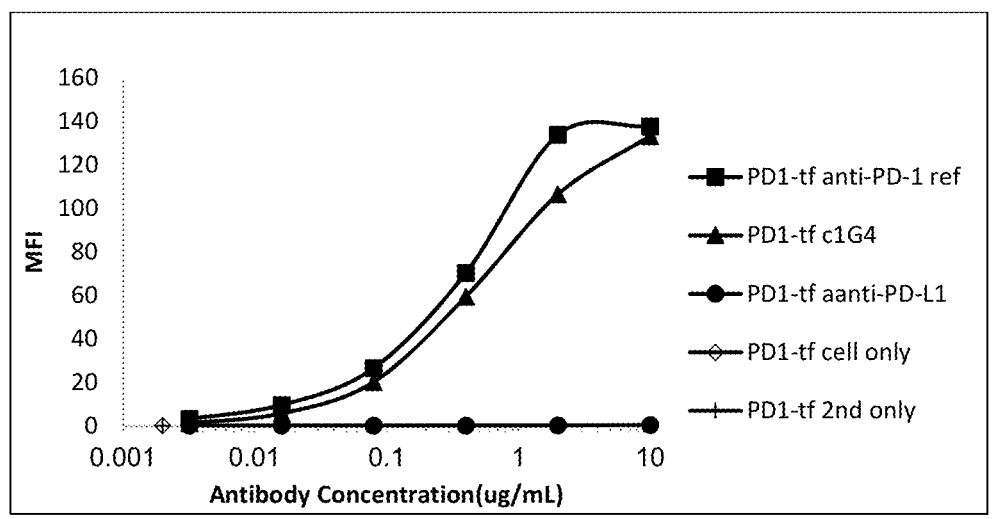

FIGS. 3A and 3B provide the binding of c1G4 antibody to CHO-S cells (FIG. 3A) and PD-1 transfected CHO-S cells (FIG. 3B) by flow cytometry. The referenced anti-PD-1 and anti-PD-L1 antibodies were used as the positive control and negative control, respectively. The results indicate that the c1G4 bound to the CHO cells transfected with PD-1 but not to CHO cells that were not transfected with human PD-1.

Figure 9:
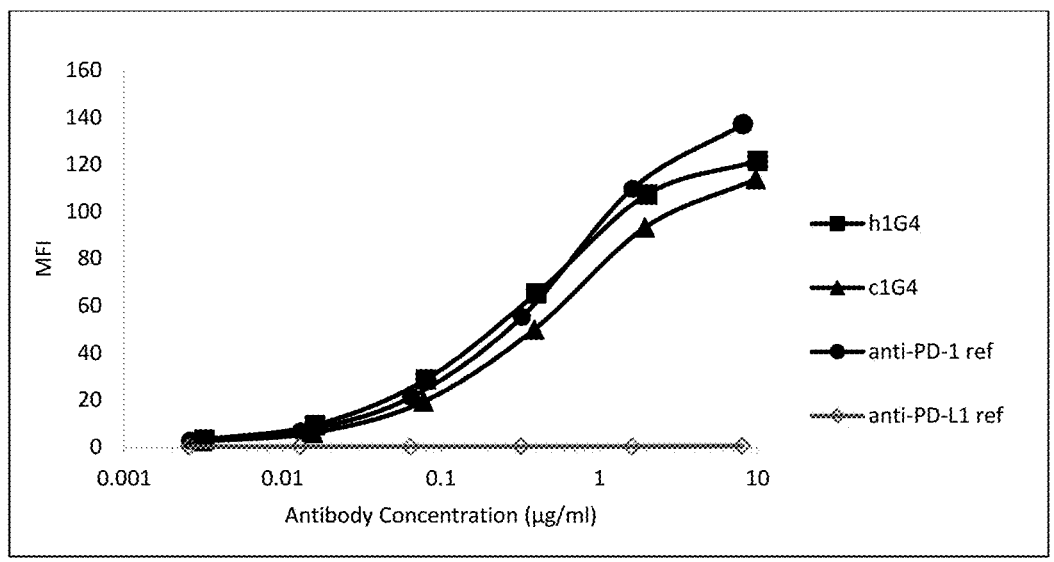
FIG. 9. Binding of humanized anti-PD-1 antibody to PD-1 expressing CHO-S cells. The binding of humanized h1G4 and original c1G4 antibody to PD-1 on the cell surface was tested by flow cytometry. The referenced anti-PD-1 and anti-PD-L1 antibodies were used as the positive control and negative control, respectively.

The binding characteristics of humanized h1G4 and original c1G4 antibody to PD-1 on the cell surface are shown in FIG. 9.

Blocking of Ligand Binding to PD-1 by Selected c1G4 and h1G4 Antibodies

Anti-PD-1 c1G4 and h1G4 were tested for the ability to block binding of the ligand PD-L1 to PD-1 expressing CHO-S cells using a flow cytometry assay. The anti-PD-1 and anti-PD-L1 antibodies were used as the positive control and negative control, respectively. PD-1 expressing CHO-S cells were suspended in FACS buffer (PBS with 1% FBS). Various concentrations of the c1G4 and h1G4 anti-PD-1 antibodies, the referenced anti-PD-1 and anti-PD-L1 antibodies were added to the cell suspension and incubated at 4° C. for 30 minutes. Unbound antibody was washed off and biotin-labeled PD-L1-Fc fusion protein was added and incubated at 4° C. for 30 minutes. The cells were washed and then stained with streptavidin-PE at 4° C. for 30 minutes. Flow cytometric analyses were performed using the Cytomics FC 500 (Beckman Coulter Inc.).

Figure 4:
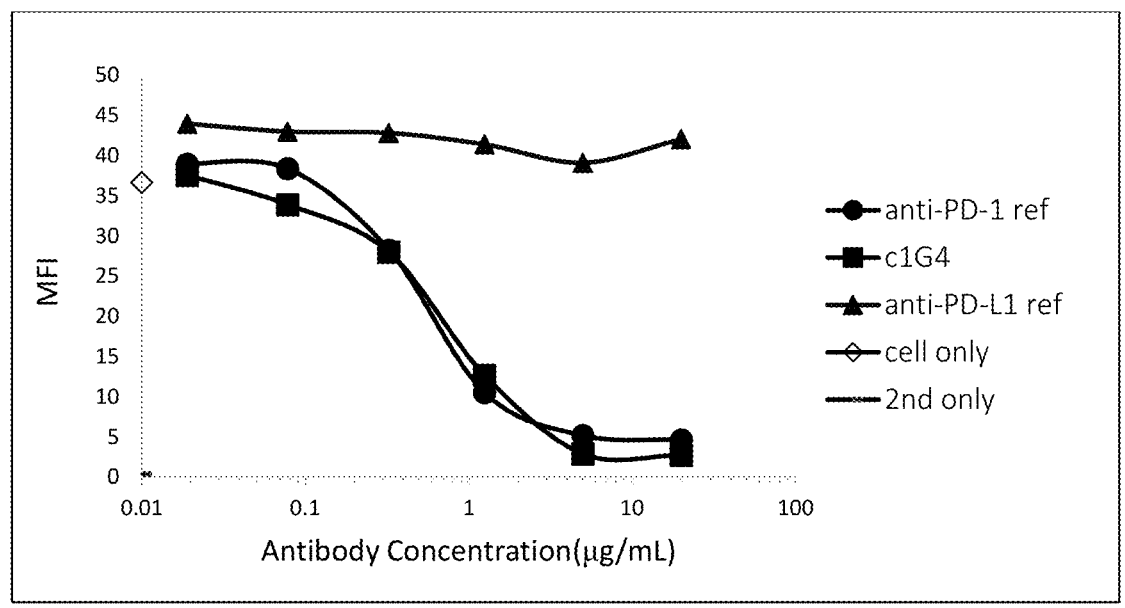
FIG. 4. Blocking of ligand binding to PD-1 by selected c1G4 antibody. Anti-PD-1 c1G4 was tested for the ability to block binding of the ligand PD-L1 to PD-1 expressing CHO-S cells using a flow cytometry assay. The referenced anti-PD-1 and anti-PD-L1 antibodies were used as the positive control and negative control, respectively. The anti-PD-1 monoclonal antibody c1G4 blocked binding of PD-L1 to PD-1 transfected CHO-S cells, as measured by the mean fluorescent intensity (MFI) of staining. These data demonstrate that the anti-PD-1 c1G4 block binding of PD-L1 ligand to cell surface PD-1.
Figure 10:
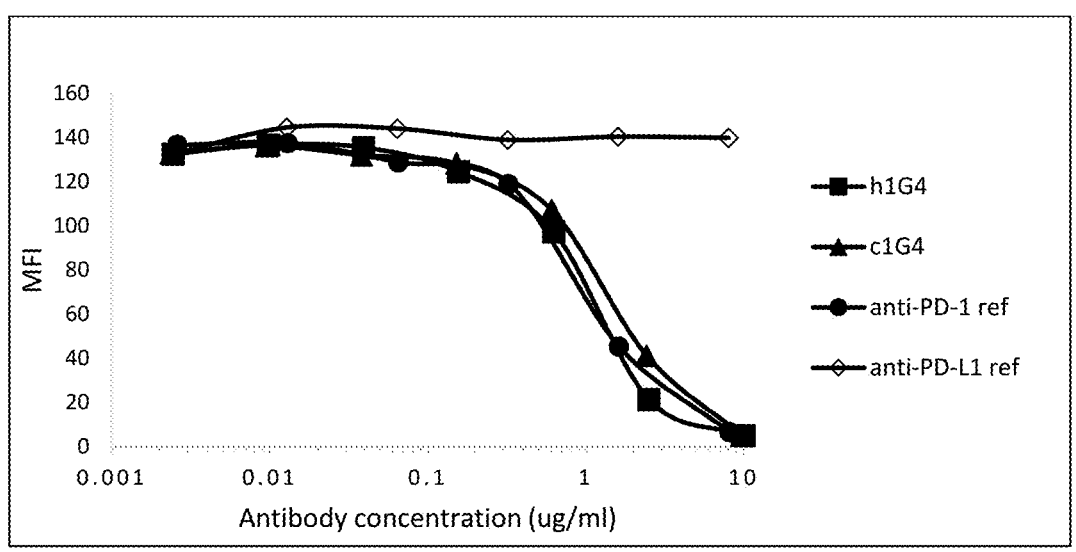
FIG. 10. Blocking of ligand binding to PD-1 by humanized h1G4 antibody. Humanized anti-PD-1 h1G4 was tested for the ability to block binding of the ligand PD-L1 to PD-1 expressing CHO-S cells using a flow cytometry assay. The referenced anti-PD-1 and anti-PD-L1 antibodies were used as the positive control and negative control, respectively. Both c1G4 and h1G4 blocked binding of PD-L1 to PD-1 transfected CHO-S cells, as measured by the mean fluorescent intensity (MFI) of staining.
Figure 11A:
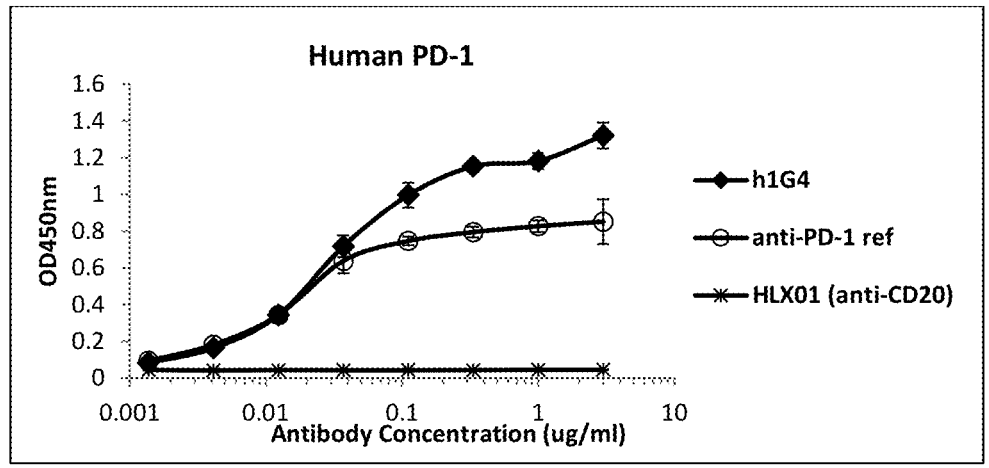
FIGS. 11A-11D illustrate species cross-reactivity of h1G4 to human (FIG. 11A), cynomolgus monkey (FIG. 11B), mouse (FIG. 11C), and rat (FIG. 11D) PD-1 proteins. All data points are the average of triplicate±SD.
Figure 11B:
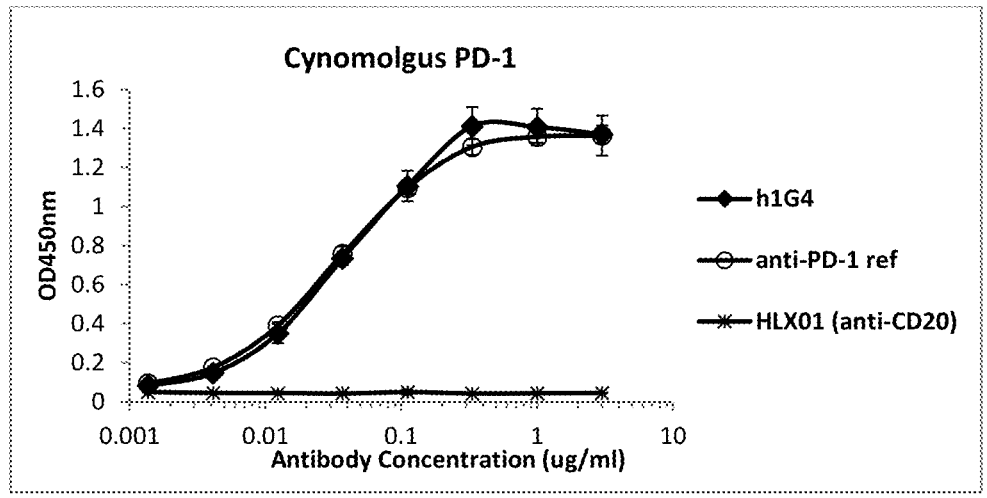
Figure 11C:
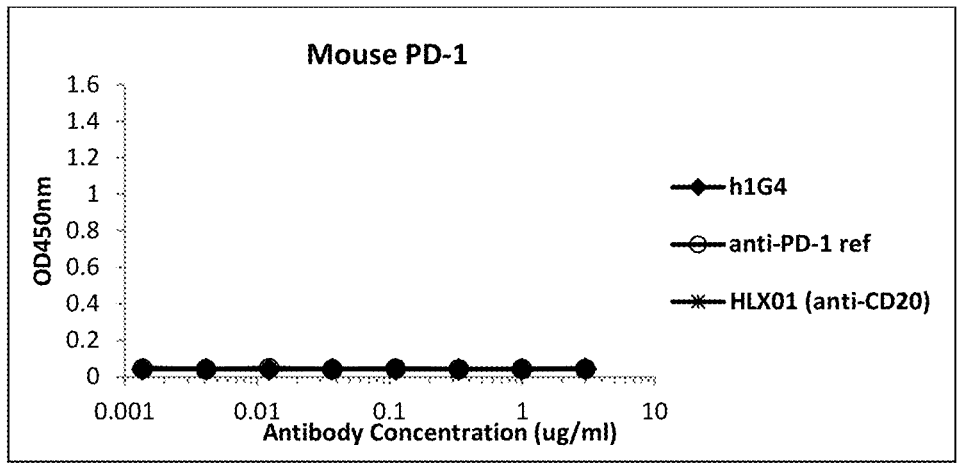
Figure 11D:
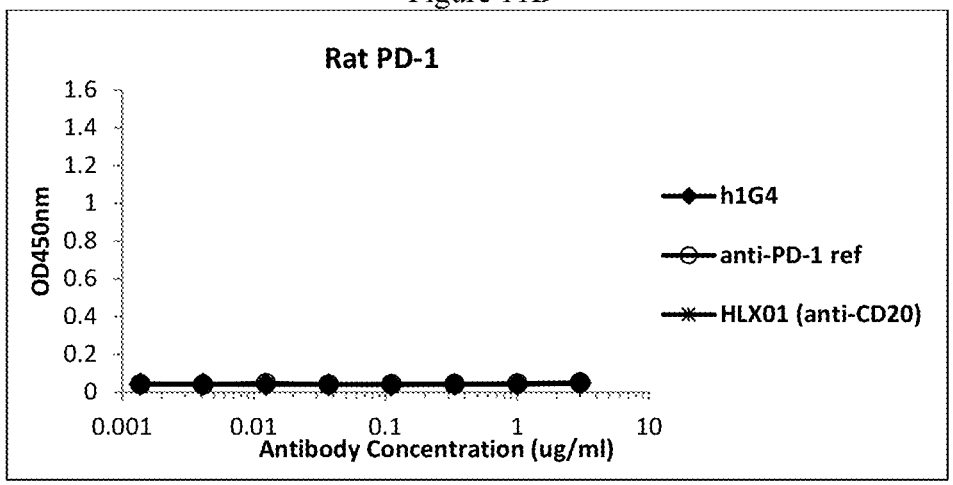

The anti-PD-1 monoclonal antibody c1G4 blocked binding of PD-L1 to PD-1 transfected CHO-S cells, as measured by the mean fluorescent intensity (MFI) of staining. These data demonstrate that both c1G4 and h1G4 blocked binding of PD-L1 to PD-1 transfected CHO-S cells, as measured by the mean fluorescent intensity (MFI) of staining (FIGS. 4 & 10).

Binding of Humanized Anti-PD-1 Antibody to Activated Human T Cell

Human T cells were isolated from PBMC using MagniSort™ Human T Cell Enrichment kit (eBioscience). Isolated T cells were activated by 5 µg/ml phytohemagglutinin (PHA) for 3 days to stimulate the PD-1 expression. Activated T cells were collected and incubating in FACS buffer (PBS with 2% FBS) with human Fc blocker (eBioscience) for 20 minutes at 4° C.

Figure 12:
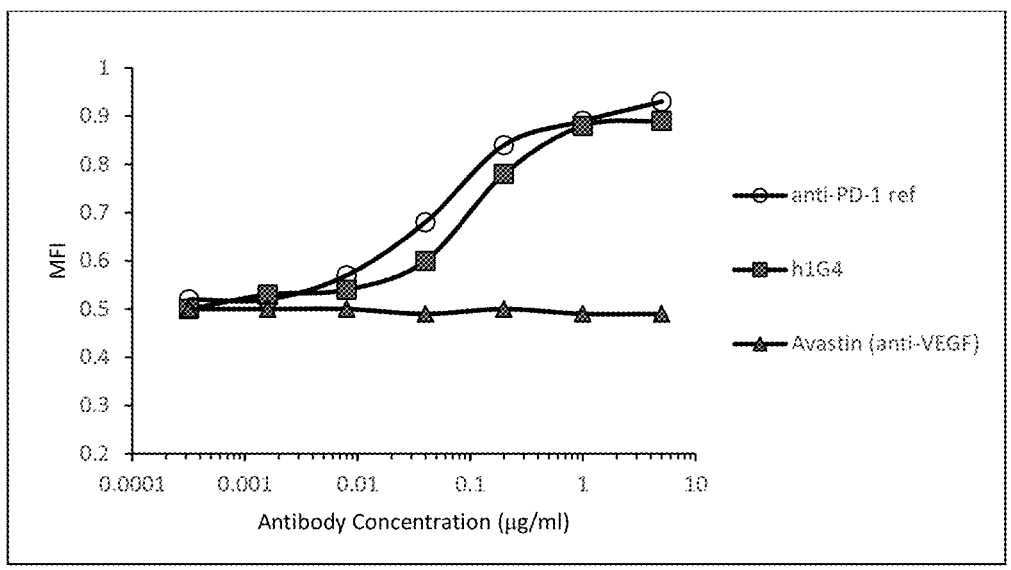
FIG. 12. Binding of humanized anti-PD-1 antibody to activated human T cells. The binding of humanized h1G4 to human T cells was tested by flow cytometry. The referenced anti-PD-1 antibody and Avastin (anti-VEGF) were used as the positive control and negative control, respectively.

Binding of anti-PD-1 monoclonal antibody was assessed by incubating the activated T cells with the serial-diluted anti-PD-1 monoclonal antibodies in FACS buffer. The cells were washed with flow buffer and the binding was detected with a FITC-labeled rabbit anti-human IgGFcγ Ab. Flow cytometric analyses were performed using the Cytomics FC 500 (Beckman Coulter Inc.). The referenced anti-PD-1 antibody and Avastin (anti-VEGF) were used as the positive control and negative control respectively The results of binding humanized anti-PD-1 antibody h1G4 to activated human T cells are shown in FIG. 12.

Example 5

Effect of Anti-PD-1 c1G4 and h1G4 on Cytokine Production in a Mixed Leukocyte Reaction (MLR)

A mixed leukocyte reaction was employed to demonstrate the effect of blocking the PD-1 pathway to lymphocyte effector cells. T cells in the assay were tested for proliferation, IFN-gamma secretion and IL-2 secretion in the presence or absence of an anti-PD-1 antibody.

Human T-cells were purified from PBMC using the Lympho-kwik T (One Lamda, Inc.). Isolated T cells were suspended in PBS and labeled with 1 µM of CFSE at room temperature for 10 minutes. After washing cells with the complete media (RPMI-1640 with 10% FBS), CFSE-labeled T cells were suspended in the complete media at the concentration of 1E6/cells.

Allogeneic dendritic cells were generated from PBMC. The isolated PBMCs were incubated with 200 U/ml of recombinant human IL-3 (eBioscience) overnight to allow monocyte/macrophage population to attach to the plates. The non-adherent cells were removed and the plates were washed twice with the complete media. The cells on the plates were then cultured in the complete media containing 200 U/ml of human IL-4 (eBioscience) and 200 U/ml of human GM-CSF (eBioscience) for 6 days. Monocyte-derived dendritic cells were matured by adding TNF-alpha (100 U/ml) to the culture at day 6 and incubating overnight. The matured DC were trypsinized, harvested, and suspended in the complete media at the concentration of 1E5/cells.

Each reaction contained $10^5$ CFSE-labeled T-cells and $10^4$ allogeneic dendritic cells in a total volume of 200 µl. Anti-PD-1 monoclonal antibodies c1G4 or h1G4 was added to each culture at different antibody concentrations. Either no antibody or an anti-VEGF antibody (Avastin) was used as a negative control. A referenced anti-PD-1 antibody was used as the positive control. The cells were cultured for 5 days at 37° C. After day 5, 100 µl of medium was taken from each culture for cytokine measurement. The levels of cytokines were measured using Human IFN-γ or IL-2 ELISA MAX™ Deluxe kits (BioLegend). The cells were collected and analyzed for T cell proliferation by flow cytometry.

Figure 5A:
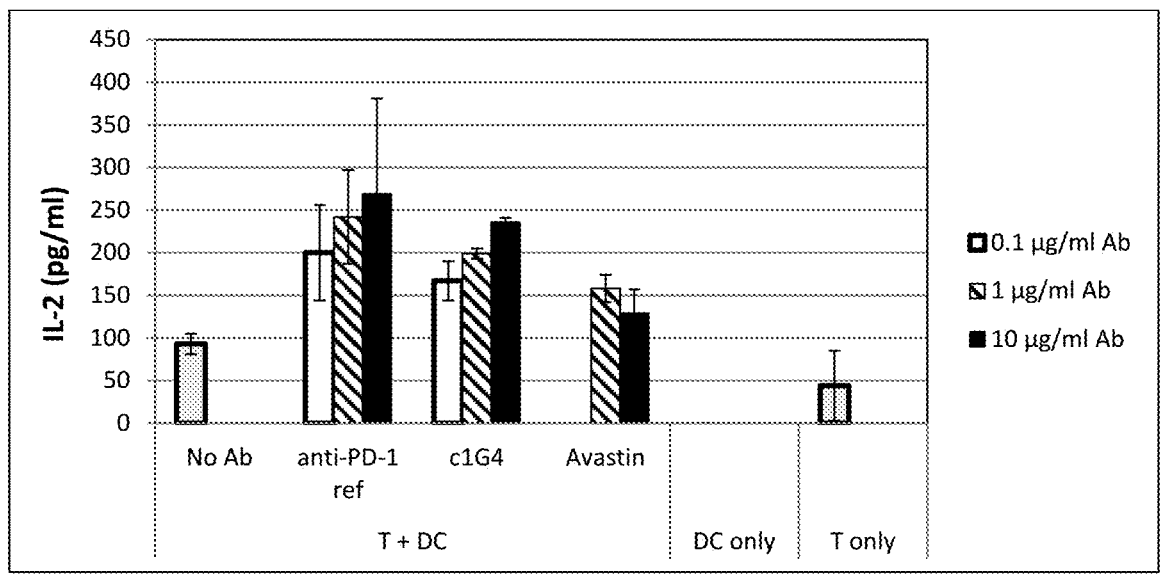
FIGS. 5A-5B. Effect of anti-PD-1 c1G4 on cytokine production in a mixed leukocyte reaction (MLR). The monoclonal antibody c1G4 against human PD-1 promotes IFN-γ secretion and IL-2 secretion in a mixed leukocyte reaction assay. The referenced anti-PD-1 and Avastin (anti-VEGF) were used as the positive control and negative control, respectively.
Figure 5B:
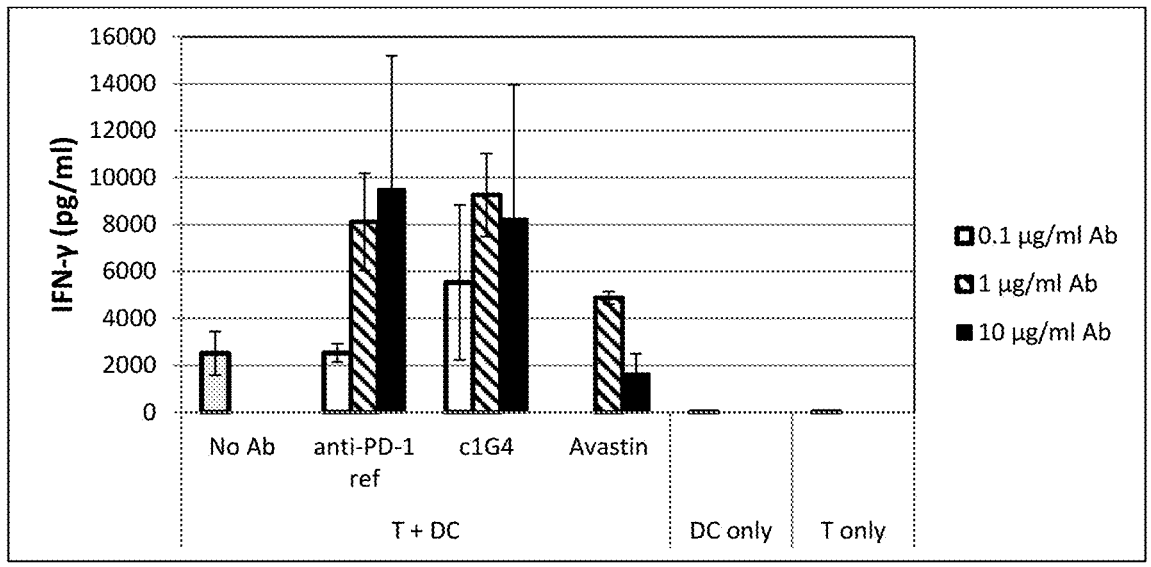

FIG. 5A illustrates concentration dependent IL-2 secretion promoted by the monoclonal antibody c1G4 against human PD-1, and FIG. 5B illustrates concentration dependent IFN-γ secretion by the monoclonal antibody c1G4 against human PD-1.

Figure 13A:
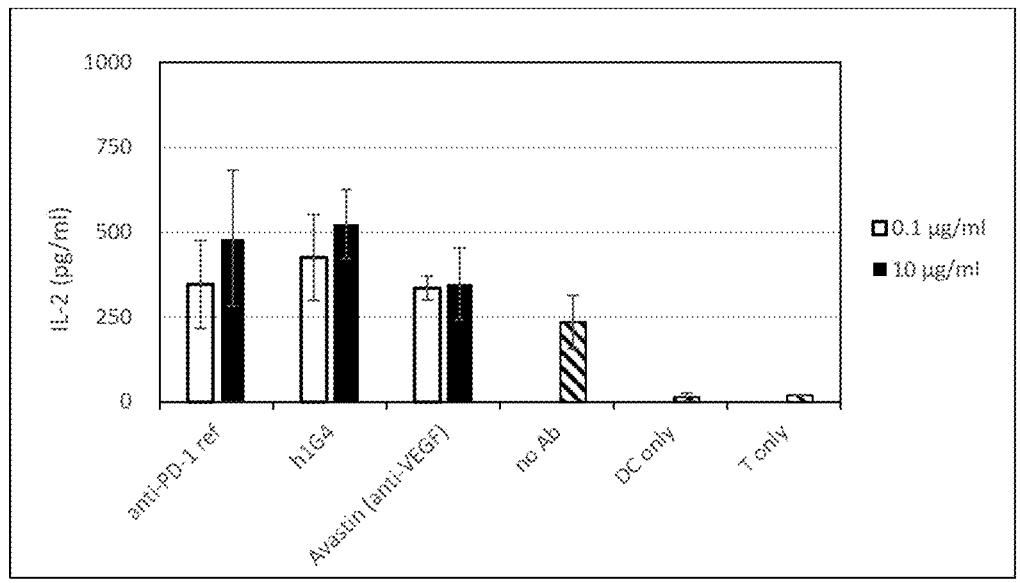
FIGS. 13A-13B. Effect of h1G4 on cytokine production in a mixed leukocyte reaction (MLR). The humanized antibody h1G4 against human PD-1 promotes IFN-γ secretion and IL-2 secretion in a mixed leukocyte reaction assay. The referenced anti-PD-1 antibody and Avastin (anti-VEGF) were used as the positive control and negative control, respectively.
Figure 13B:
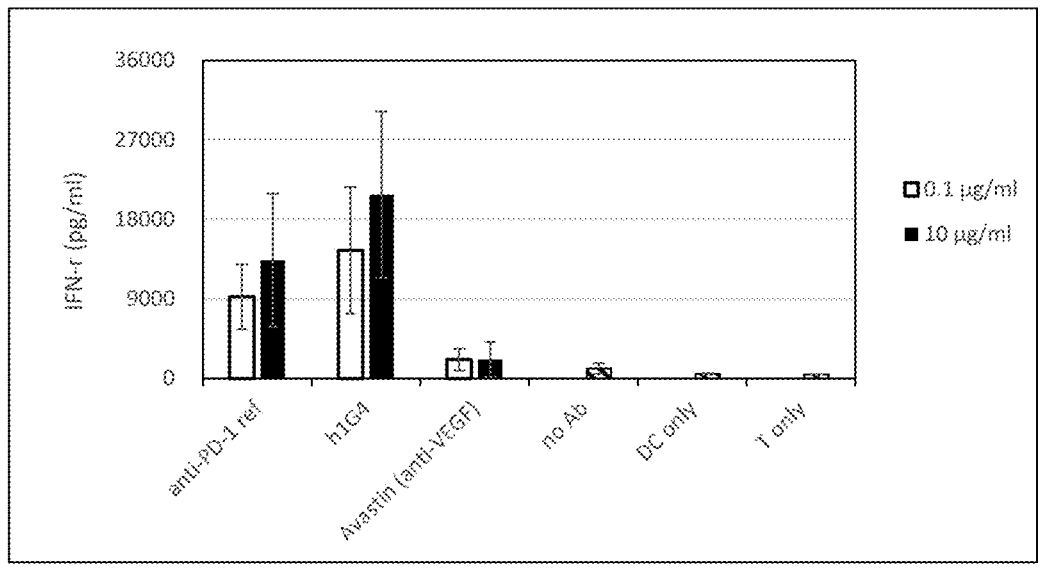

FIG. 13A illustrates concentration dependent IL-2 secretion promoted by the monoclonal antibody h1G4 against human PD-1, and FIG. 13B illustrates concentration dependent IFN-γ secretion by the monoclonal antibody h1G4 against human PD-1.

Figure 6A:
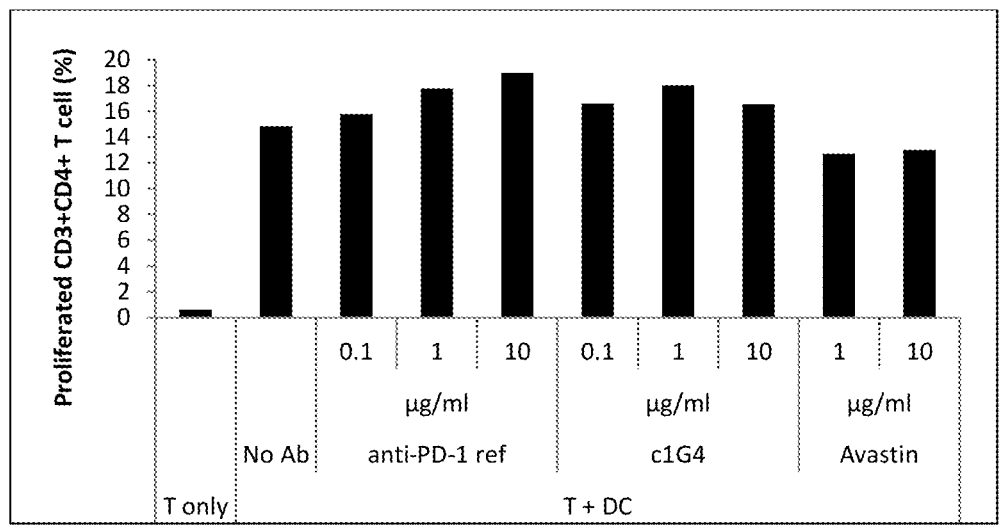
FIGS. 6A-6B. Effect of anti-PD-1 c1G4 on T cell proliferation in a mixed leukocyte reaction (MLR). The monoclonal antibody c1G4 against human PD-1 promotes $CD4^+$ and $CD8^+$ T cell proliferation in a mixed leukocyte reaction assay. The referenced anti-PD-1 and Avastin (anti-VEGF) were used as the positive control and negative control, respectively.
Figure 6B:
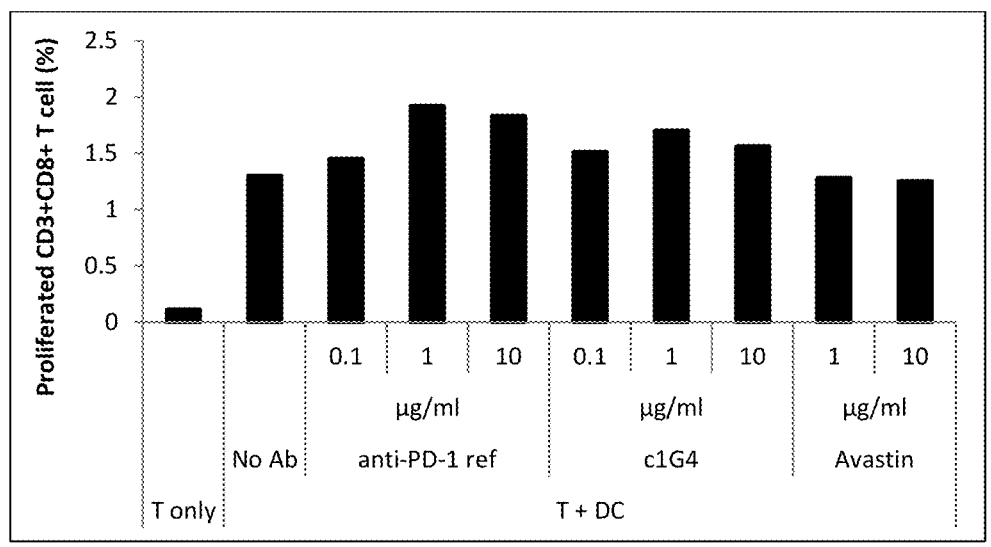
Figure 14A:
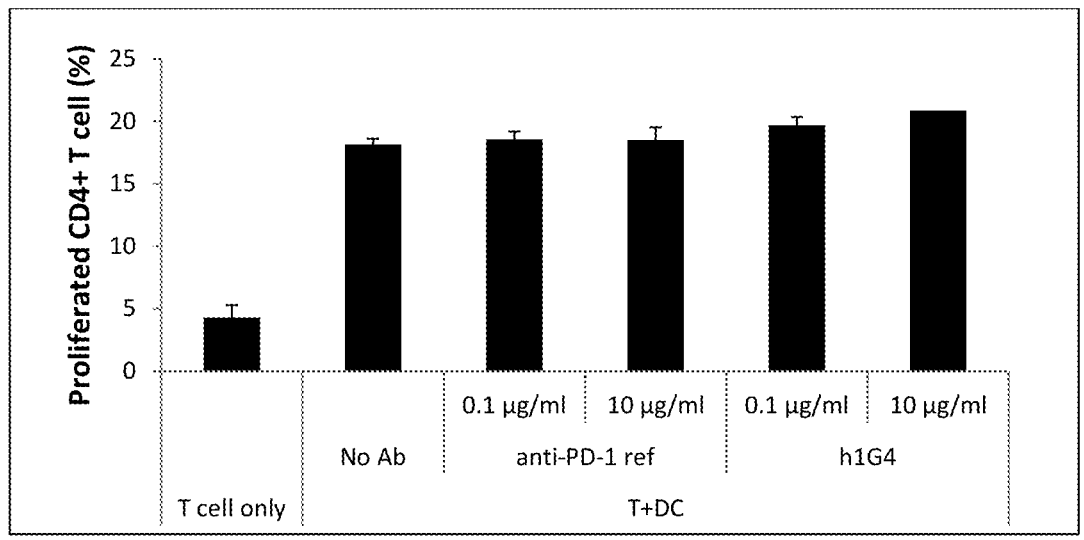
FIGS. 14A-14B. Effect of h1G4 on T cell proliferation in a mixed leukocyte reaction (MLR). The humanized antibody h1G4 against human PD-1 promotes $CD4^+$ and $CD8^+$ T cell proliferation in a mixed leukocyte reaction assay. The referenced anti-PD-1 antibody and Avastin (anti-VEGF) were used as the positive control and negative control, respectively.
Figure 14B:
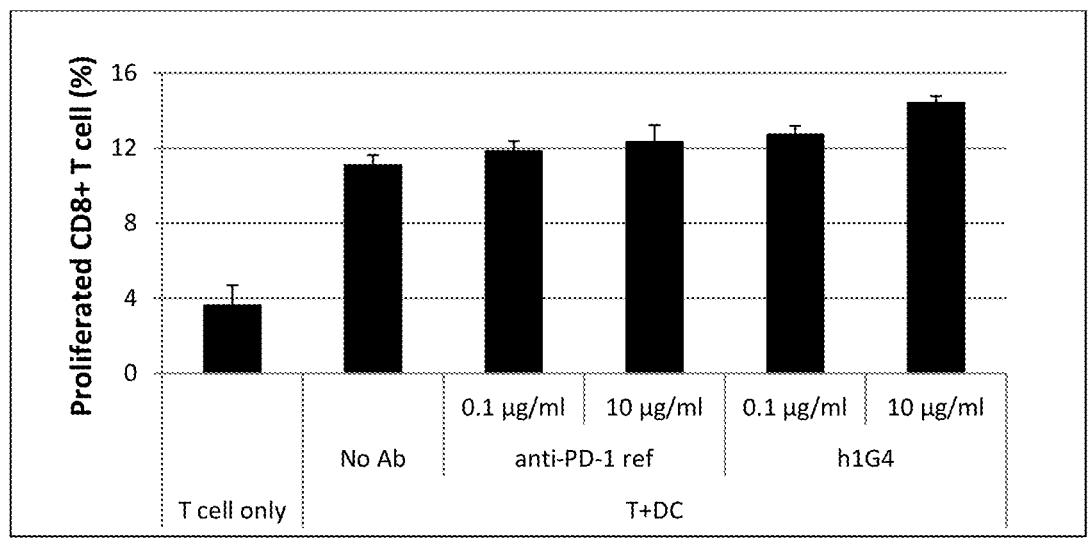

The monoclonal antibody c1G4 against human PD-1 promotes CD4$^+$ and CD8$^+$ T cell proliferation in a mixed leukocyte reaction assay. FIG. 6A illustrates the CD4$^+$ T cell proliferation at various concentration of c1G4 antibodies, and FIG. 6B illustrates the CD8$^+$ T cell proliferation at various concentration of c1G4 antibodies. FIG. 14A illustrates the CD4$^+$ T cell proliferation at various concentration of h1G4 antibodies, and FIG. 14B illustrates the CD8$^+$ T cell proliferation at various concentration of h1G4 antibodies.

In summary, these results indicate that the anti-PD-1 monoclonal antibodies c1G4 and h1G4 promote T-cell proliferation, IFN-gamma secretion and IL-2 secretion. In contrast, cultures containing the negative control antibody did not show an increase in T cell proliferation, IFN-gamma or IL-2 secretion.

Example 6

Tumor Growth Inhibition Activity of c1G4 and h1G4 Antibodies

The in vivo activity of anti-human PD-1 antibodies was investigated in xenograft mouse models using immunocompromised NOD/SCID (non-obese diabetic/severe combined immunodeficiency) mice. Cancer cells and isolated human PBMC were mixed immediately before subcutaneous administration at the indicated effector-to-target (E:T) ratio. Each mouse was bilaterally inoculated with the mixtures of cancer cells and human PBMC. Four mice were assigned to each experimental group. The first dose of the test article was administered intraperitoneally 1 day after engraftment of cancer/effector cells. The mice received doses of the test article twice a week for 3-4 weeks. The formation of tumor was observed in each animal two times a week. Tumors were measured by caliper and tumor volumes (V) were calculated using the following formula:

$$V(mm^3)=0.5\times(\text{length(mm)}\times\text{width(mm)}\times\text{width (mm)}/2).$$

Figure 7A:
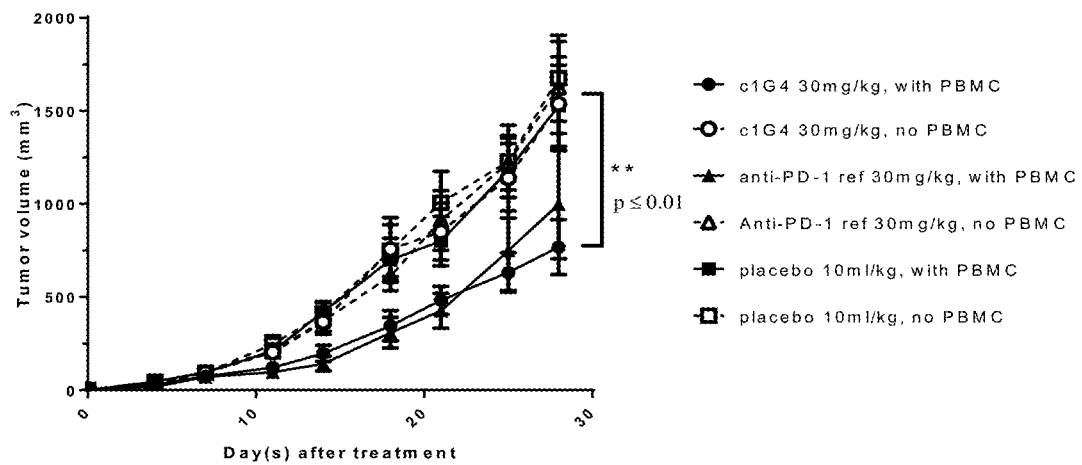
FIGS. 7A-7B. Tumor Growth Inhibition Activity of c1G4 antibody. The mice (n=4/group) were engrafted subcutaneously with the mixture of human colon cancer cell lines HT29 and freshly isolated human PBMC (cancer cells: PBMC=2:1). Anti-PD-1 antibodies were intraperitoneally injected into mice twice a week from day 1. Tumor growth curves were shown in FIG. 7A. The individual tumor volume at day 28 were presented in FIG. 7B. All data points are the means±SEM.
Figure 7B:
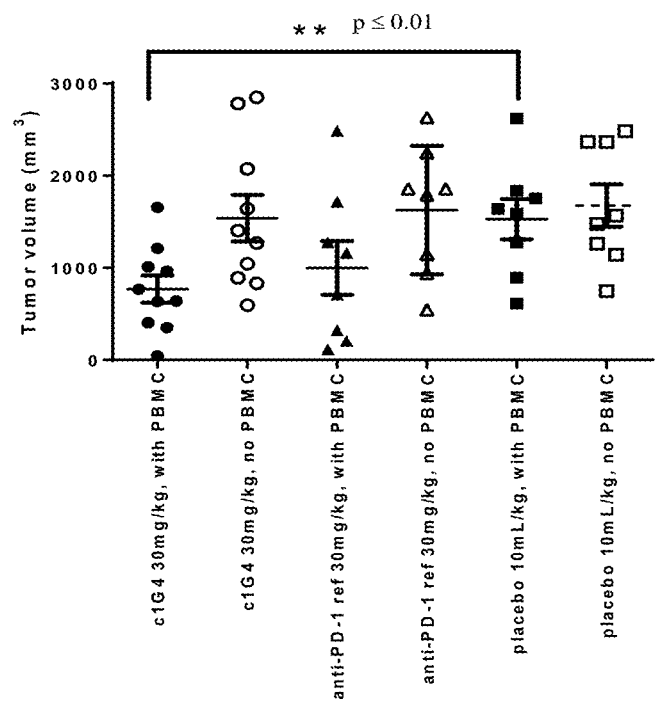
Figure 15A:
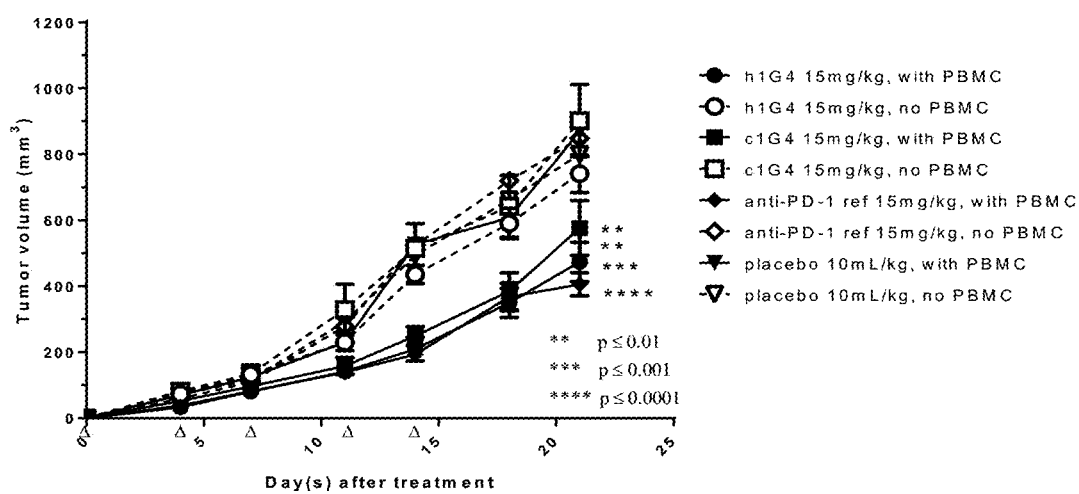
FIGS. 15A-15B. Tumor Growth Inhibition Activity of h1G4 antibody in HT29/PBMC xenograft model. The mice (n=4/group) were engrafted subcutaneously with the mixture of human colon cancer cell lines HT29 and freshly isolated human PBMC (cancer cells: PBMC=3:1). Anti-PD-1 antibodies were intraperitoneally injected into mice twice a week from day 1. Tumor growth curves were shown in FIG. 15A. The individual tumor volume at day 21 were presented in FIG. 15B. All data points are the means±SEM.
Figure 15B:
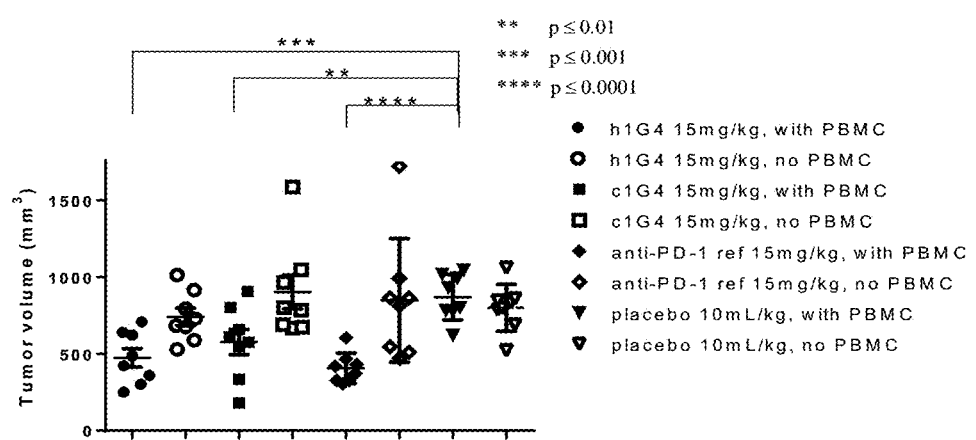
Figure 16A:
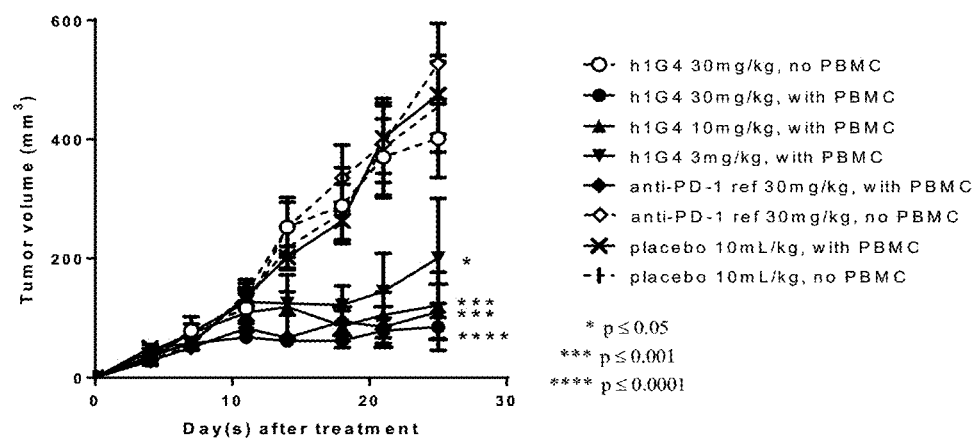
FIGS. 16A-16B. Tumor Growth Inhibition Activity of h1G4 antibody in NCI-H292/PBMC xenograft model. The mice (n=4/group) were engrafted subcutaneously with the mixture of human NSCLC cell lines NCI-H292 and freshly isolated human PBMC (cancer cells: PBMC=3:1). Anti-PD-1 antibodies were intraperitoneally injected into mice twice a week from day 1. Tumor growth curves were shown in FIG. 16A. The individual tumor volume at day 25 were presented in FIG. 16B. All data points are the means±SEM.
Figure 16B:
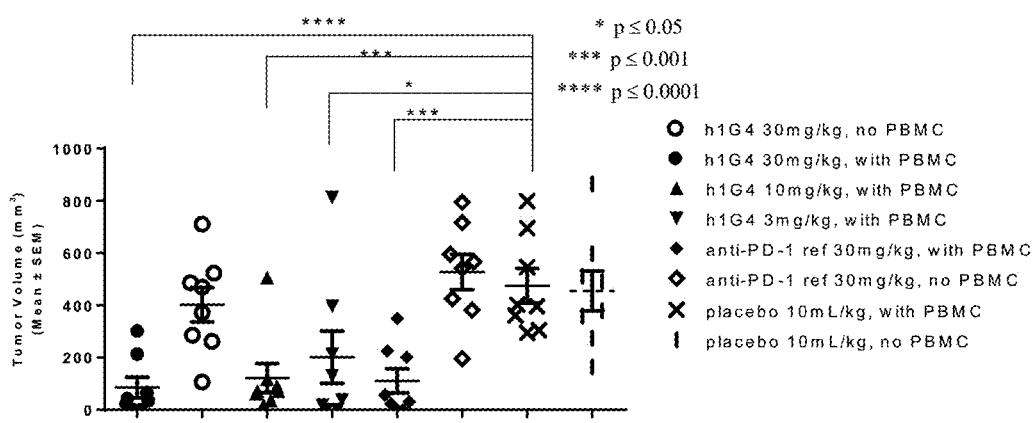

Tumor growth curves with c1G4 or h1G4 antibodies in HT29/PBMC xenograft model were shown in FIGS. 7A and 15A, respectively. The individual tumor volume at day 28 with c1G4 or day 21 with h1G4 HT29/PBMC xenograft model were presented in FIGS. 7B and 15B, respectively. Furthermore, tumor growth curves with h1G4 antibody in NCI-H292/PBMC were shown in FIG. 16A. The individual tumor volume at day 25 with h1G4 antibody were presented in FIG. 16B. All data points are the means±SEM.

Figure 21:
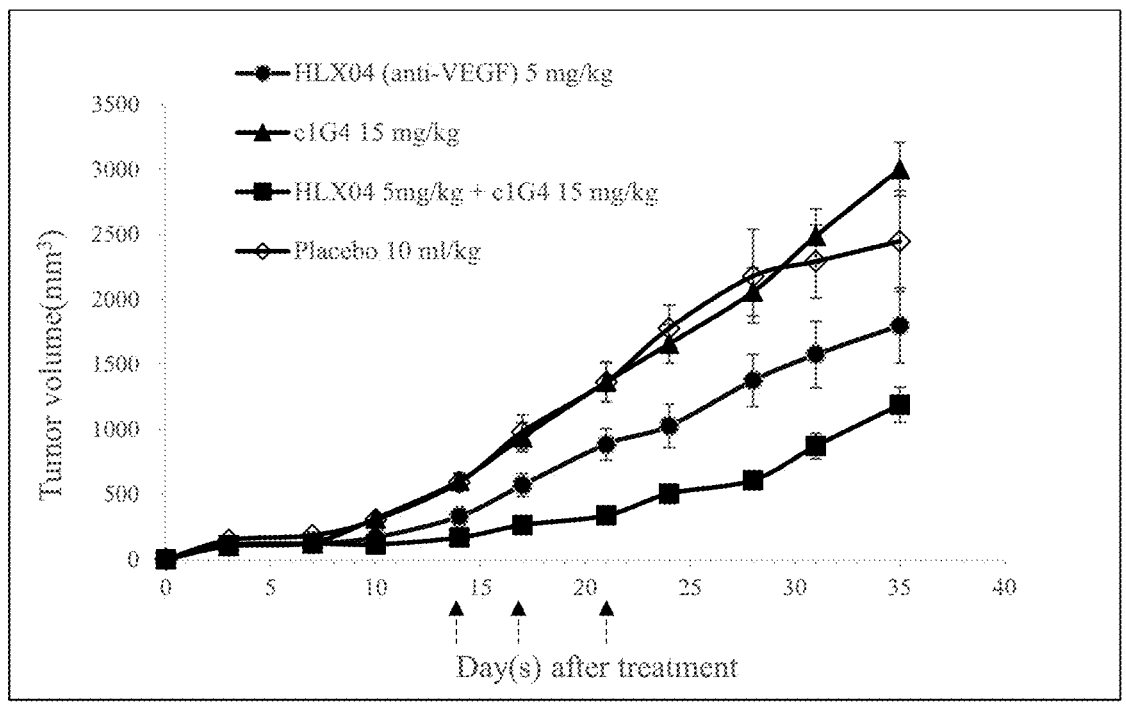
FIG. 21. The combination of anti-PD-1 and anti-VEGF monoclonal antibody in HT29/PBMC xenograft model. The mice (n=4/group) were engrafted subcutaneously with the mixture of human colon cancer cell line HT29 and freshly isolated human PBMC (cancer cells: PBMC=3:1). Anti-PD-1 mAb, anti-VEGF mAb (HLX04), or anti-PD-1 mAb plus anti-VEGF mAb were intraperitoneally injected into mice. The dosing days were indicated by arrows. The tumor volume was measured twice a week. All data points are the means±SEM.

Furthermore, the combination therapy of anti-PD-1 and anti-VEGF monoclonal antibody in HT29/PBMC xenograft model was also studied. The data indicating an enhanced tumor inhibition with the combination of anti-PD-1 and anti-VEGF are presented in FIG. 21.

Example 7

Species Cross-Reactivity of h1G4

The recombinant human, rat, mouse, and cynomolgus monkey PD-1 fusion proteins were purchased from Sino Biological Inc. PD-1/Fc (9 ng per well) were immobilized onto 96-well assay plat by incubating overnight at 4° C. Nonspecific binding sites were blocked using 5% skim milk in PBS for one hour at room temperature. After washing plates three times with PBST, indicated concentrations of h1G4, the referenced anti-PD-1 (positive control), and HLX01 (negative control) were incubated with the immobilized proteins for one hour at room temperature. The plates were washed three times with PBST and then incubated for one hour at room temperature with peroxidase-labeled goat anti-human IgG F(ab)′$_2$ (Jackson ImmunoResearch Laboratories) diluted 1/10,000 in PBS. After washing, plates were developed using TMB (eBioscience). The absorbance was read at the wavelength of 450 nm by Vmax microplate reader (MolecularDevices).

FIGS. 11A-11D show species cross-reactivity of h1G4 to human (FIG. 11A), cynomolgus monkey (FIG. 11B), mouse (FIG. 11C), and rat (FIG. 11D) PD-1 proteins.

Example 8

Tumor Growth Inhibition Activity of h1G4 Antibody

Tumor Growth Inhibition Activity of h1G4 Antibody in hPD1 KI Mice

The in vivo activity of anti-human PD-1 antibodies was investigated in human PD-1 knock-in C57BL/6 mice (hPD1 KI mice). The mice were subcutaneously inoculated with human PD-L1 transfected mouse colon cancer cells (1E6 cells per mouse). Antibody treatments were started when tumor volumes reached approximately 75 mm3 (Day 9). Four animals were assigned to each experimental group before the treatment. The animals received doses of anti-PD-1 antibodies twice a week for 3-4 weeks. The formation of tumor was observed in each animal two times a week.

Figure 17:
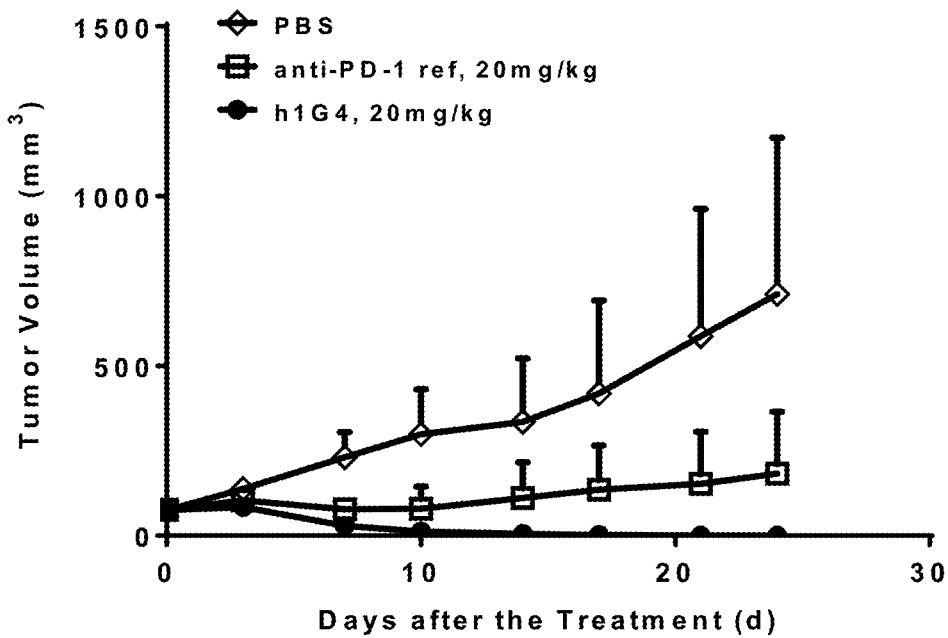
FIG. 17. Tumor Growth Inhibition Activity of h1G4 antibody in hPD1 KI mice. The human PD-1 knock-in (hPD1 KI) mice (n=4/group) were engrafted subcutaneously with MC38-huPD-L1 (MC38 transfected with human PD-L1) cells. Antibody treatments were started when tumor volumes reached approximately 75 mm3. Anti-PD-1 antibodies were intraperitoneally injected into mice twice a week. All data points are the means±SD.

Tumors were measured by caliper and tumor volumes (V) were calculated using the following formula: V (mm³)=0.5× (length (mm)×width (mm)×width (mm)/2). Tumor Growth Inhibition Activity of h1G4 antibody in hPD1 KI mice is shown in FIG. 17.

Efficacy Study of h1G4 in a Triple-Negative Breast Cancer (TNBC) Cell Line Xenograft Model in Humanized NSG Mice Humanized NSG mice (NOD.Cg-Prkdcscid IL2rgtm1Wjl/SzJ) were subcutaneously inoculated with MDA-MB-231 (human triple-negative breast cancer cell line). Mice were randomized into 3 groups (n=9/group) based on tumor volume according to the table when tumor volumes reach ~60-150 mm³. Mice were dosed intraperitoneally with h1G4 once every 7 days on study days 0, 7, 14, 21, and 28. Keytruda (anti-PD-1) were intraperitoneal injected once every 5 days on study days 0, 5, 10, 15, and 20. The formation of tumor was observed in each animal every 3-4 days. Tumors were measured by caliper and tumor volumes (V) were calculated using the following formula:

$$V(mm3)=0.5\times(\text{length(mm)}\times\text{width(mm)}\times\text{width(mm)}/2)$$

Figure 18:
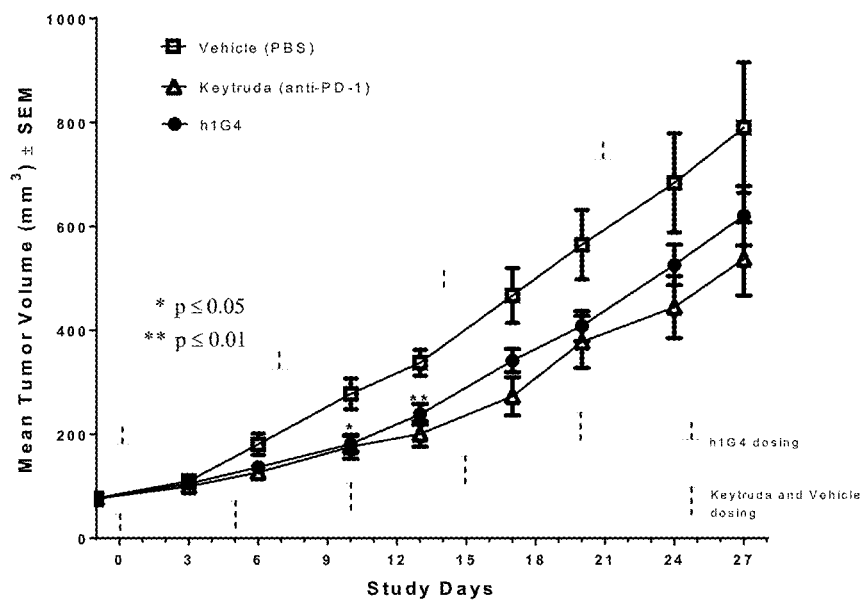
FIG. 18. Efficacy Study of h1G4 in a triple-negative breast cancer (TNBC) cell line xenograft model in humanized NSG mice. Humanized NSG mice (n=9/group) were subcutaneously inoculated with MDA-MB-231 cells. Antibody treatments were started when tumor volumes reached approximately 60-150 mm$^3$. The dosing days were indicated by arrows. All data points are the means±SEM.

FIG. 18 illustrates efficacy study of h1G4 in a triple-negative breast cancer (TNBC) cell line xenograft model in humanized NSG mice.

Example 9

Determination of Equilibrium Dissociation Constant (KD) of Affinity Matured Anti-PD-1 Antibodies 33B, 66E, and 711D The humanized anti-PD-1 antibody h1G4 was used in in vitro phage display-based affinity maturation experiments to generate clones with improved binding performance. Both CDR-L1/CDR-L3/CDR-H3 (focusing on 3 CDRs) and CDR-L1/CDR-L2/CDR-L3/CDR-H1/CDR-H2/CDR-H3 (focusing on 6 CDRs) nucleic acid libraries of h1G4 were generated via PCR, cloned into a phage display vector, and transformed into *E. coli* TG1 or SS320 cells to produce a library of phages. After three rounds of panning with biotinylated PD-1-His coupled to streptavidin-coated magnetic Dynabeads® M-280 (Thermo Fisher Scientific #11205D) for both libraries, three Fab clones, i.e., 33B, 66E and 711D, were screened via ELISA. Further kinetic characteristics were measured by surface plasmon resonance (SPR) (see the same SPR method as described above for FIG. 9) using full-length IgGs of 33B, 66E and 711D and found to have binding performance that was equivalent to or better than the referenced anti-PD-1 antibody.

Table 5 shows an amino acid sequence of the CDRs of 33B, 66E, and 711D screened from phage-display based affinity maturation in comparison with h1G4.

TABLE 5

| CDR | L1 | L2 | L3 |
|---|---|---|---|
| h1G4 | KASQDVTTAVA (SEQ ID NO: 9) | WASTRHT (SE ID NO: 10) | QQHYTIPWT (SEQ ID NO: 11) |
| 33B | KASTDVTTAVA (SEQ ID NO: 15) | WASLRHT (SEQ ID NO: 16) | QQHYGIPWT (SEQ ID NO: 17) |
| 66E | KAKQDVTTAVA (SEQ ID NO: 21) | WASTRHT (SEQ ID NO: 10) | QQHYWIPWT (SEQ ID NO: 22) |
| 711D | KASQDVTNAVA (SEQ ID NO: 24) | WASTRHT (SEQ ID NO: 10) | QQHYTIPWT (SEQ ID NO: 11) |

TABLE 5-continued

| | H1 | H2 | H3 |
|---|---|---|---|
| H1G4 | FTFSNYGMS (SEQ ID NO: 12) | TISGGGSNIY (SEQ ID NO: 13) | VSYYYGIDF (SEQ ID NO: 14) |
| 33B | F<u>R</u>FSNYGMS (SEQ ID NO: 18) | TISGGGSN<u>A</u>Y (SEQ ID NO: 19) | <u>T</u>SYYYGIDF (SEQ ID NO: 20) |
| 66E | FTFSNYGMS (SEQ ID NO: 12) | TISGGGSNIY (SEQ ID NO: 13) | VSYYYGID<u>L</u> (SEQ ID NO: 23) |
| 711D | FTFSNYGMS (SEQ ID NO: 12) | TISGGGSNIY (SEQ ID NO: 13) | <u>S</u>SYYYGID<u>L</u> (SEQ ID NO: 25) |

Table 6 shows association and dissociation kinetics, along with calculated affinity (KD) of 33B, 66E, and 711D measured by surface plasmon resonance (SPR). Improvement of affinity of anti-PD-1 antibodies in contrast to the referenced anti-PD-1 antibody was also shown in Table 6. Data are representative of two independent experiments performed in duplicate.

TABLE 6

| Average (n = 2) | ka [1/(M · s)] | kd [1/s] | KD [M] | Improvement |
|---|---|---|---|---|
| Anti-PD-1 ref | 4.91E+05 | 1.49E−03 | 3.05E−09 | 1.00 |
| h1G4 | 4.57E+05 | 2.16E−04 | 4.79E−10 | 6.37 |
| c1G4 | 5.50E+05 | 1.77E−04 | 3.25E−10 | 9.38 |
| 33B | 2.90E+05 | 8.44E−04 | 2.91E−09 | 1.05 |
| 66E | 4.74E+05 | 4.66E−04 | 9.79E−10 | 3.12 |
| 711D | 4.72E+05 | 2.50E−04 | 5.34E−10 | 5.71 |

Example 10

Functions of Affinity Matured Antibodies Effect of Human Anti-PD-1 Antibodies (33B, 66E an 711D) on Cytokine Production in a Mixed Leukocyte Reaction (MLR)

Figure 19A:
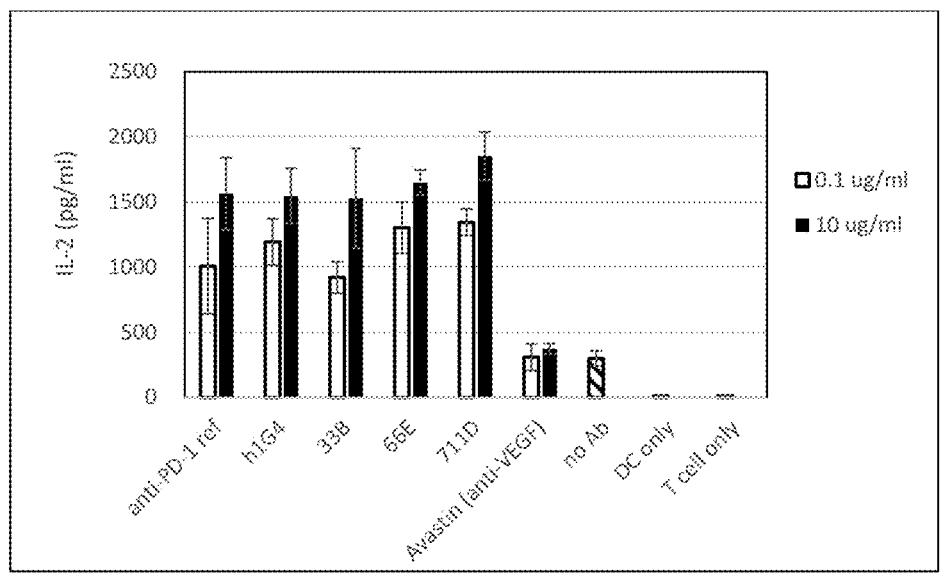
FIGS. 19A-19B. Effect of human anti-PD-1 antibodies on cytokine production in a mixed leukocyte reaction (MLR). The human monoclonal antibodies against human PD-1 promotes IFN-γ secretion and IL-2 secretion in a mixed leukocyte reaction assay. The referenced anti-PD-1 antibody and Avastin (anti-VEGF) were used as the positive control and negative control, respectively.
Figure 19B:
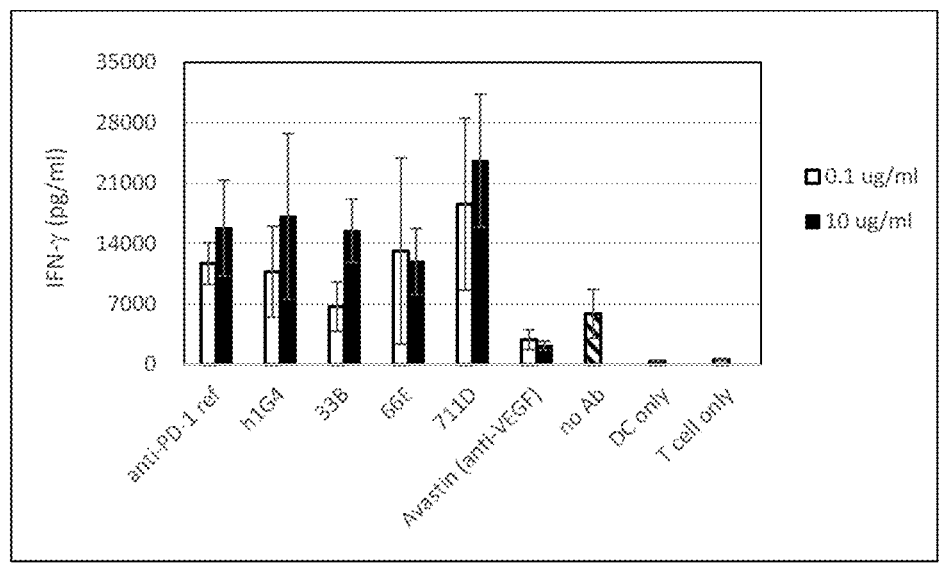

Followed the same method as described above, this study shows that the human monoclonal antibodies against human PD-1, such as 66E and 711D, promote IFN-γ secretion and IL-2 secretion in a mixed leukocyte reaction assay. The referenced anti-PD-1 antibody and Avastin (anti-VEGF) were used as the positive control and negative control, respectively. FIG. 19A illustrates concentration dependent IL-2 secretion by the affinity matured antibodies, and FIG. 19B illustrates concentration dependent IFN-γ secretion the affinity matured antibodies.

Figure 20:
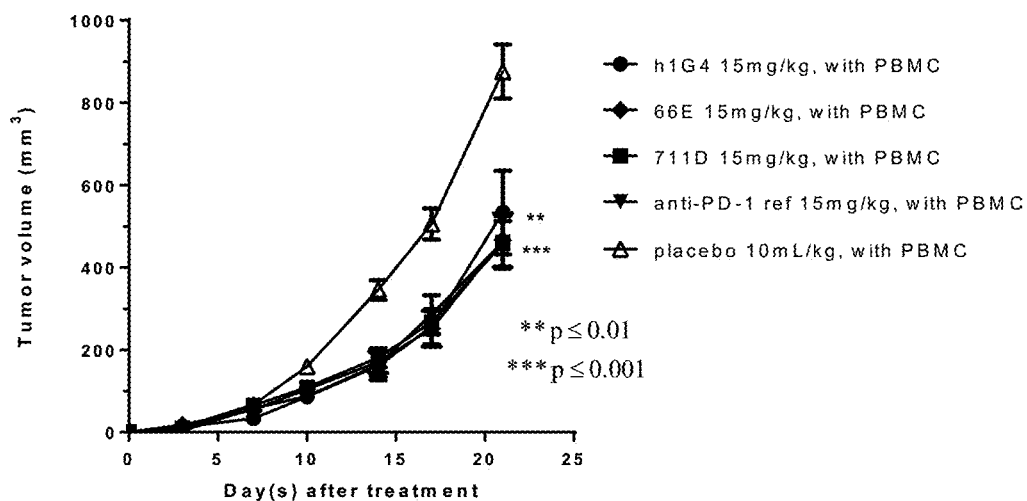
FIG. 20. Tumor growth inhibition activity of human anti-PD-1 antibodies in HT29/PBMC xenograft model. The mice (n=4/group) were engrafted subcutaneously with the mixture of human colon cancer cell line HT29 and freshly isolated human PBMC (cancer cells: PBMC=3:1). Anti-PD-1 antibodies were intraperitoneally injected into mice twice a week from day 1. The tumor volume was measured twice a week. All data points are the means±SEM.

Tumor Growth Inhibition Activity of Human Anti-PD-1 Antibodies in HT29/PBMC Xenograft model Followed the same method as described above, the mice (n=4/group) were engrafted subcutaneously with the mixture of human colon cancer cell line HT29 and freshly isolated human PBMC (cancer cells: PBMC=3:1). Anti-PD-1 antibodies were intraperitoneally injected into mice twice a week from day 1. The tumor volume was measured twice a week. Tumor growth inhibition activity of human affinity matured anti-PD-1 antibodies in HT29/PBMC xenograft model is shown in FIG. 20. All data points are the means±SEM.

Example 11

PD-1 Combination Therapies

The in vivo activity of combination therapy with anti-PD-1 and other therapeutic antibodies was investigated in xenograft mouse models using immunocompromised NOD/SCID (non-obese diabetic/severe combined immunodeficiency) mice. Cancer cells and isolated human PBMC were mixed immediately before subcutaneous administration at the indicated effector-to-target (E:T) ratio. Each mouse was bilaterally inoculated with the mixtures of cancer cells and human PBMC. Four or five animals were assigned to each experimental group. The first dose of the test article was administered intraperitoneally 1 day after engraftment of cancer/effector cells. The animals received doses of the test article twice a week for 3-4 weeks. The formation of tumor was observed in each animal two times a week. Tumors were measured by caliper and tumor volumes (V) were calculated using the following formula:

$$V(mm^3)=0.5\times(length(mm)\times width(mm)\times width(mm)/2)$$

Figure 22A:
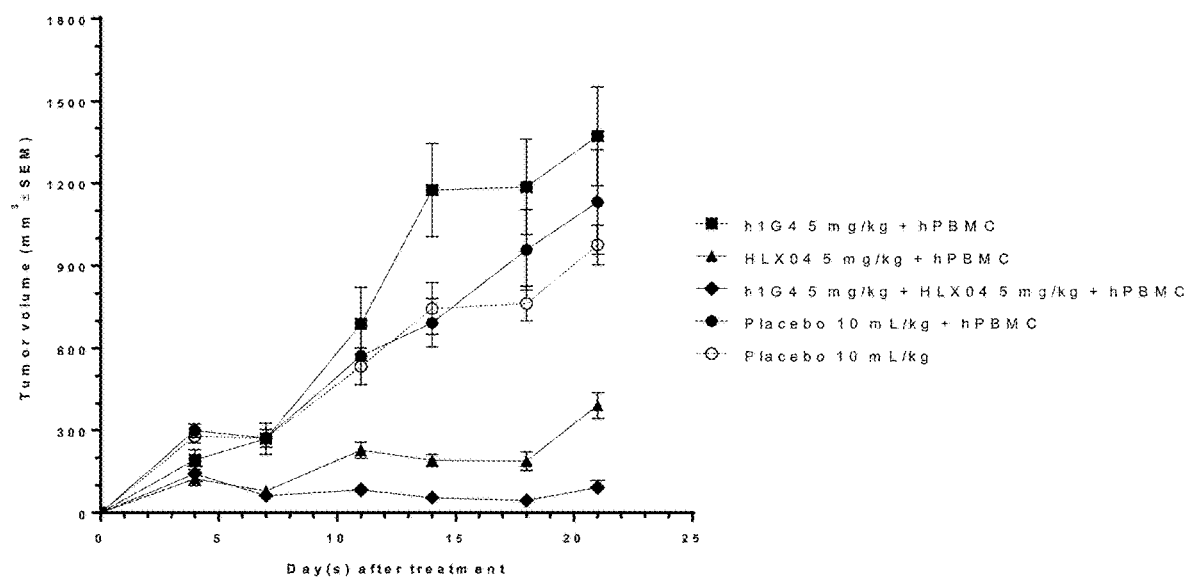
FIGS. 22A-22B. Tumor Growth Inhibition Activity of anti-PD-1 mAb plus anti-VEGF mAb in NSCLC xenograft mice model. The mice (n=4/group) were engrafted subcutaneously with the mixture of human NSCLC cells NCI-H292 and freshly isolated human PBMC (cancer cells: PBMC=3:1). Anti-PD-1 (h1G4), and anti-VEGF (HLX04) antibodies were intraperitoneally injected into mice twice a week from day 1. Tumor growth curves were shown in FIG. 22A. The individual tumor volume at day 21 were presented in FIG. 22B. All data points are the means±SEM.
Figure 22B:
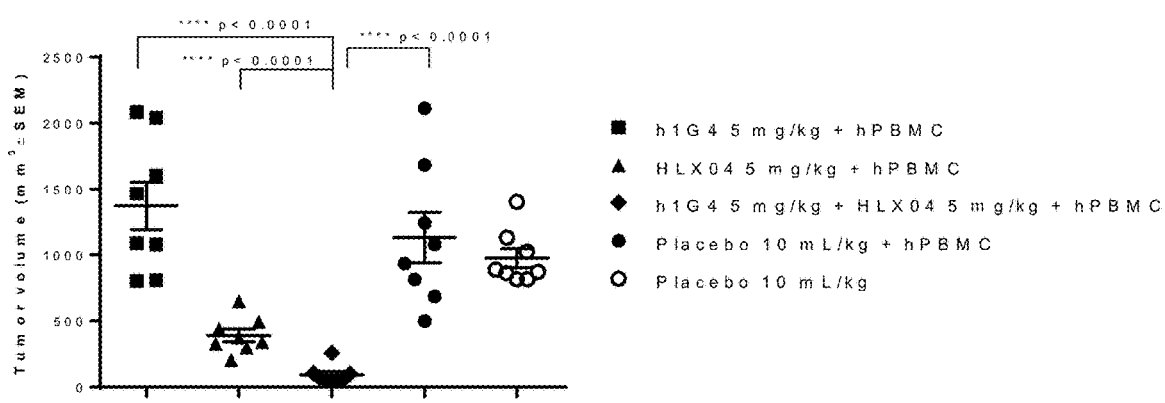

Tumor Growth Inhibition Activity of Anti-PD-1 mAb Plus Anti-VEGF mAb in NSCLC Xenograft Mice Model In these studies, the mice (n=4/group) were engrafted subcutaneously with the mixture of human NSCLC cells NCI-H292 and freshly isolated human PBMC (cancer cells: PBMC=3:1). Anti-PD-1 (h1G4), and anti-VEGF (HLX04) antibodies were intraperitoneally injected into mice twice a week from day 1. Tumor growth curves were shown in FIG. 22A. The individual tumor volume at day 21 were presented in FIG. 22B. All data points are the means±SEM. These data illustrate that anti-PD-1 mAb, h1G4, in combination with anti-VEGF mAb, HLX04, suppresses tumor growth of NCI-H292 xenografts more effectively than either agent used alone.

Figure 23A:
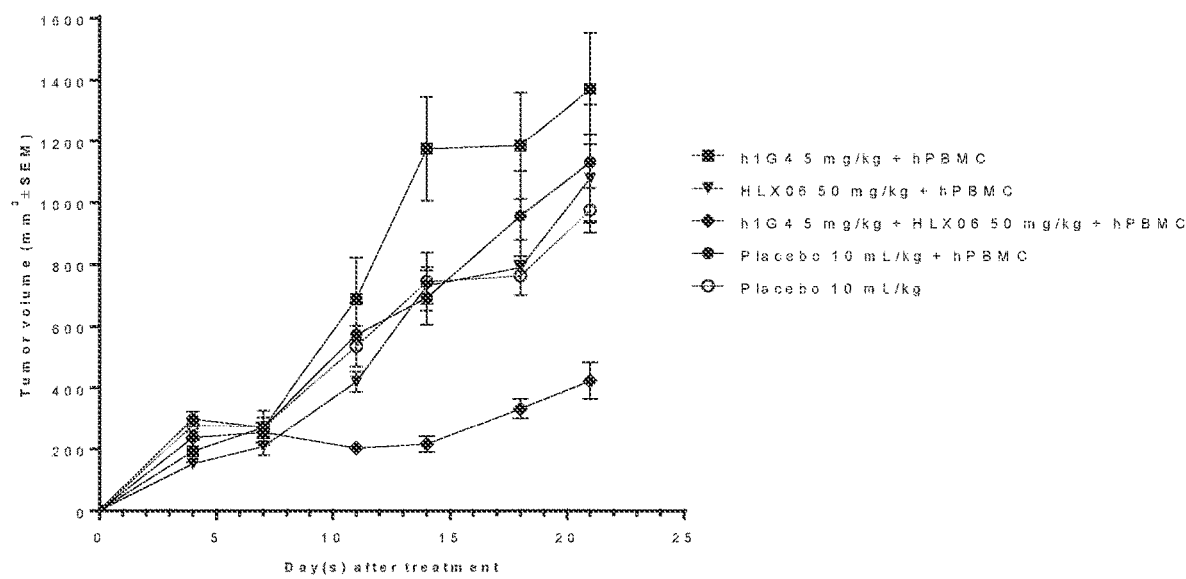
FIGS. 23A-23B. Tumor Growth Inhibition Activity of anti-PD-1 mAb plus anti-VEGFR2 mAb in NSCLC xenograft mice model. The mice (n=4/group) were engrafted subcutaneously with the mixture of human NSCLC cells NCI-H292 and freshly isolated human PBMC (cancer cells: PBMC=3:1). Anti-PD-1 (h1G4), and anti-VEGFR2 (HLX06) antibodies were intraperitoneally injected into mice twice a week from day 1. Tumor growth curves were shown in FIG. 23A. The individual tumor volume at day 21 were presented in FIG. 23B. All data points are the means±SEM.
Figure 23B:
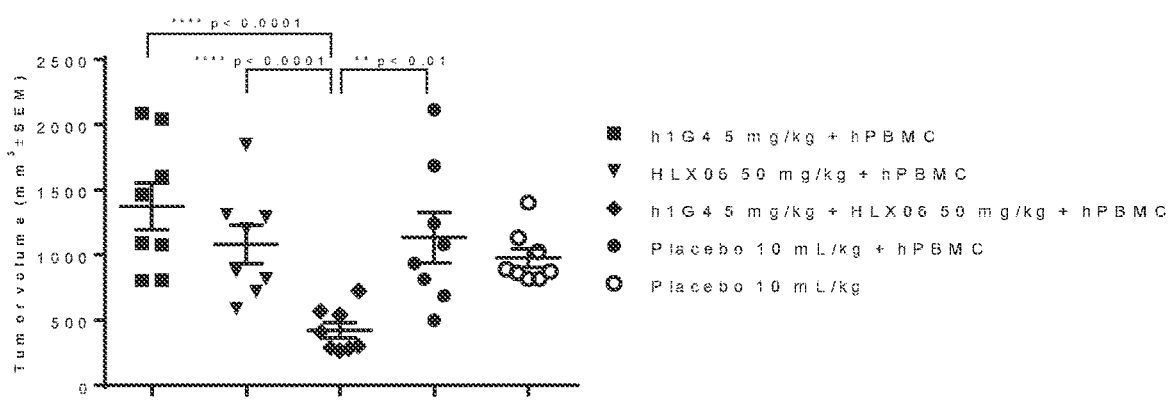

In other studies, the mice (n=4/group) were engrafted subcutaneously with the mixture of human NSCLC cells NCI-H292 and freshly isolated human PBMC (cancer cells: PBMC=3:1). Anti-PD-1 (h1G4), and anti-VEGFR2 (HLX06) antibodies were intraperitoneally injected into mice twice a week from day 1. Tumor growth curves were shown in FIG. 23A. The individual tumor volume at day 21 were presented in FIG. 23B. All data points are the means±SEM. These data illustrate that anti-PD-1 mAb, h1G4, in combination with anti-VEGFR2 mAb, HLX06, suppresses tumor growth of NCI-H292 xenografts more effectively than either agent used alone.

Figure 24A:
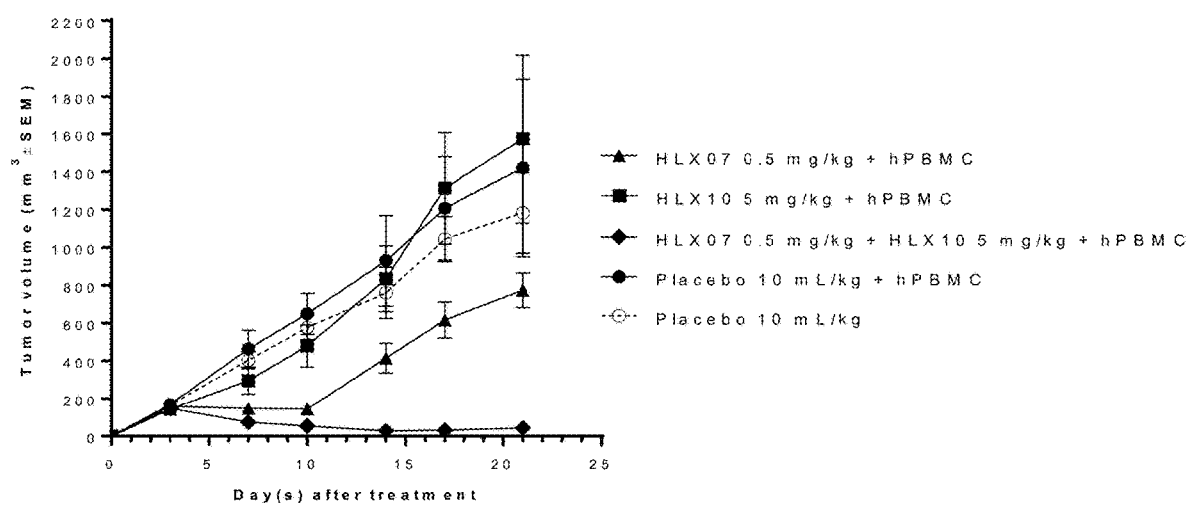
FIGS. 24A-24B. Tumor Growth Inhibition Activity of anti-PD-1 mAb plus anti-EGFR mAb in NSCLC xenograft mice model. The mice (n=4/group) were engrafted subcutaneously with the mixture of human NSCLC cells NCI-H292 and freshly isolated human PBMC (cancer cells: PBMC=3:1). Anti-PD-1 (HLX10), and anti-EGFR (HLX07) antibodies were intraperitoneally injected into mice twice a week from day 1. Tumor growth curves were shown in FIG. 24A. The individual tumor volume at day 21 were presented in FIG. 24B. All data points are the means±SEM.
Figure 24B:
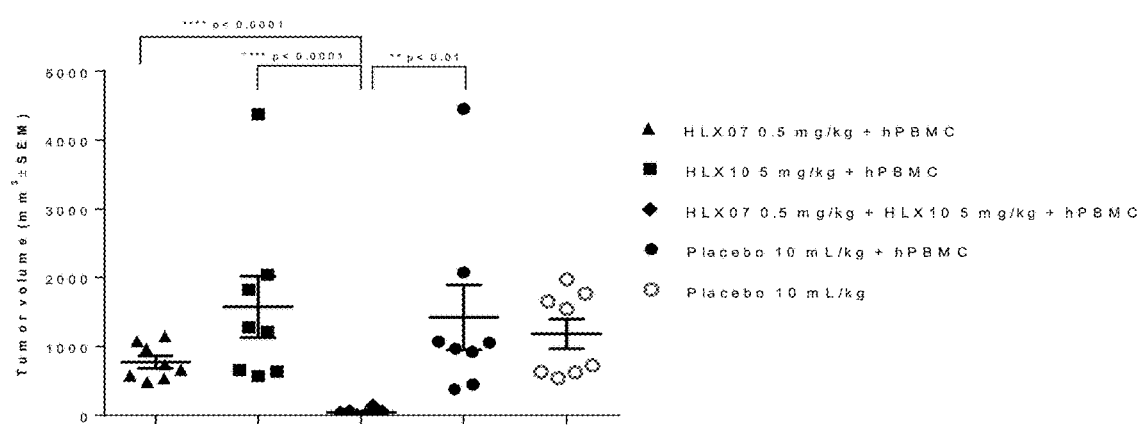

Tumor Growth Inhibition Activity of Anti-PD-1 mAb Plus Anti-EGFR mAb in NSCLC Xenograft Mice Model Followed the same method as described above, the mice (n=4/group) were engrafted subcutaneously with the mixture of human NSCLC cells NCI-H292 and freshly isolated human PBMC (cancer cells: PBMC=3:1). Anti-PD-1 (HLX10), and anti-EGFR (HLX07) antibodies were intraperitoneally injected into mice twice a week from day 1. Tumor growth curves were shown in FIG. 24A. The individual tumor volume at day 21 were presented in FIG. 24B. All data points are the means±SEM. These data indicate that anti-PD-1 mAb, HLX10 (h1G4), in combination with anti-EGFR mAb, HLX07, suppresses tumor growth of NCI-H292 xenografts more effectively than either agent used alone.

Figure 25A:
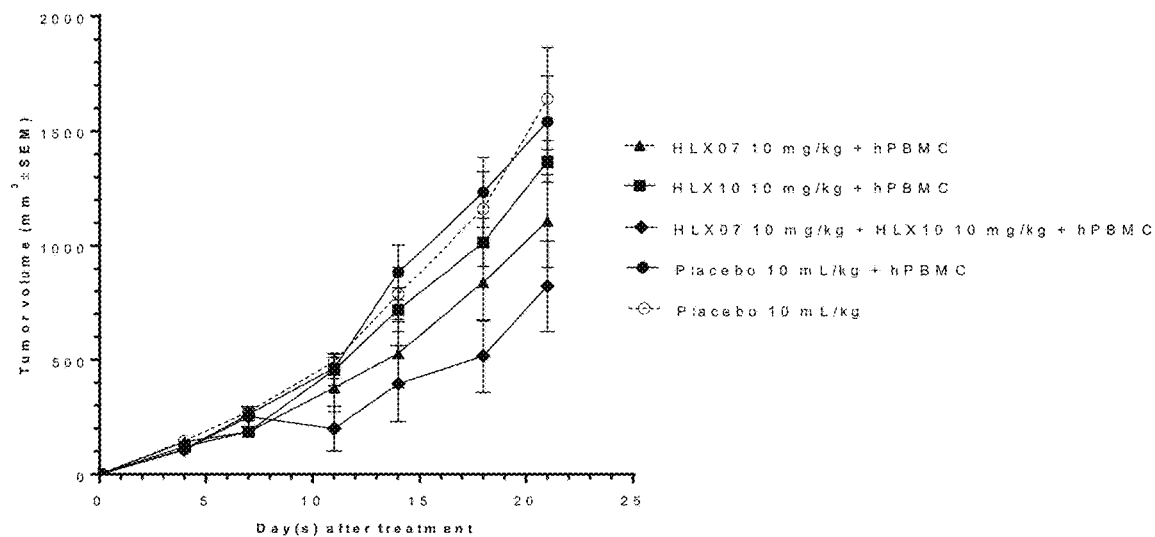
FIGS. 25A-25B. Tumor Growth Inhibition Activity of anti-PD-1 mAb plus anti-EGFR mAb in HT-29 (KRAS$^{WT}$, BRAF$^{V600E}$) xenograft mice model. The mice (n=5/group) were engrafted subcutaneously with the mixture of human colon cancer cells HT-29 and freshly isolated human PBMC (cancer cells: PBMC=3:1). Anti-PD-1 (HLX10), and anti-EGFR (HLX07) antibodies were intraperitoneally injected into mice twice a week from day 1. Tumor growth curves were shown in FIG. 25A. The individual tumor volume at day 21 were presented in FIG. 25B. All data points are the means±SEM.
Figure 25B:
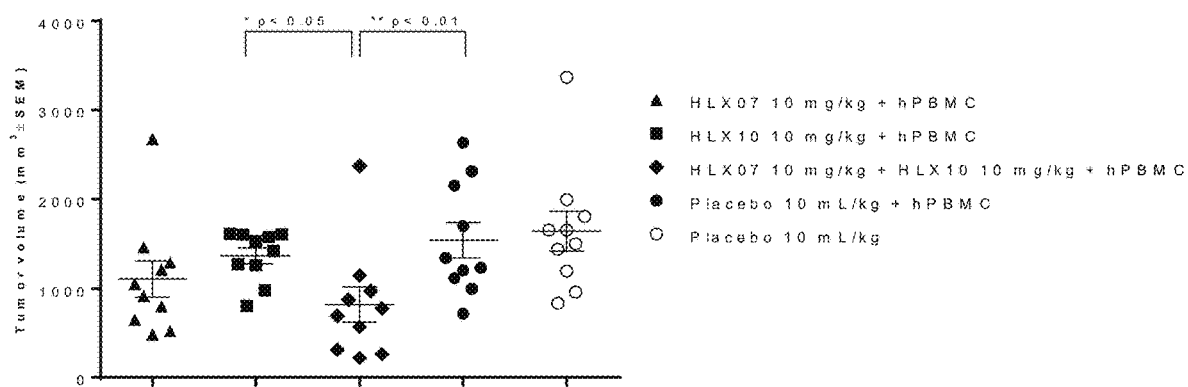

Further, the mice (n=5/group) were engrafted subcutaneously with the mixture of human colon cancer cells HT-29 and freshly isolated human PBMC (cancer cells: PBMC=3:1). Anti-PD-1 (HLX10), and anti-EGFR (HLX07) antibodies were intraperitoneally injected into mice twice a week from day 1. Tumor growth curves were shown in FIG. 25A. The individual tumor volume at day 21 were presented in FIG. 25B. All data points are the means±SEM.

These data indicate that Anti-PD-1 mAb, HLX10 (h1G4), in combination with anti-EGFR mAb, HLX07, suppresses tumor growth of BRAF mutant HT-29 xenografts more effectively than HLX10 used alone. HLX10 plus HLX07 treatment produces slightly greater inhibition of tumor growth than HLX07 treatment alone. The average tumor growth inhibition rate of HLX10 plus HLX07 treatment and HLX07 treatment alone were 47% and 28%, respective.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

The invention claimed is:

1. An anti-PD-1 antibody comprising an amino acid sequence selected from the group consisting of:
   (a) a light chain variable domain ($V_L$) sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14);
   (b) a light chain variable domain ($V_L$) sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain variable domain ($V_H$) sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20);
   (c) a light chain variable domain ($V_L$) sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain variable ($V_H$) domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23); and
   (d) a light chain variable domain ($V_L$) sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

2. The anti-PD-1 antibody of claim 1, which is a Fab, Fab', a F(ab)'2, a single-chain Fv (scFv), a Fv fragment, or an IgG.

3. The anti-PD-1 antibody of claim 1, which is a diabody, a linear antibody, or a multispecific antibody.

4. The anti-PD-1 antibody of claim 1, which is conjugated to a label selected from the group consisting of a radioisotope, a fluorescent dye, and an enzyme.

5. The anti-PD-1 antibody of claim 1, which is conjugated to a therapeutic agent selected from the group consisting of an anti-neoplastic agent, a chemotherapeutic agent, a growth inhibitory agent and a cytotoxic agent.

6. A composition comprising an anti-PD-1 antibody and a pharmaceutically acceptable carrier, wherein the anti-PD-1 antibody comprises:
   (a) a light chain variable domain ($V_L$) sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14);
   (b) a light chain variable domain ($V_L$) sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain variable domain ($V_H$) sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20);

(c) a light chain variable domain ($V_L$) sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain variable ($V_H$) domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23); or (d) a light chain variable domain ($V_L$) sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

7. A method of treating cancer in a subject expressing PD-1, comprising administering to the subject an effective amount of a composition comprising an anti-PD-1 antibody and a pharmaceutically acceptable carrier, wherein the anti-PD-1 antibody comprises:

a. a light chain variable domain ($V_L$) sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14);

b. a light chain variable domain ($V_L$) sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain variable domain ($V_H$) sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20);

c. a light chain variable domain ($V_L$) sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain variable ($V_H$) domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23); or d. a light chain variable domain ($V_L$) sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

8. The method of claim 7, wherein the cancer is selected from the group consisting of melanoma, NSCLC, head and neck, urothelial cancer, triple-negative breast cancer (TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer, esophageal cancer, nasopharyngeal carcinoma (NPC), biliary tract cancer, colorectal cancer, breast cancer, cervical cancer, thyroid cancer, and salivary cancer.

9. The method of claim 7, wherein the subject is further administered one or more therapeutic antibody selected from the group consisting of an anti-VEGF antibody, an anti-VEGFR2 antibody, and an anti-EGFR antibody.

10. The method of claim 7, wherein the subject is further treated with a radiation therapy or a surgery.

11. The method of claim 9, wherein the subject is further treated with a radiation therapy or a surgery.

12. The method of claim 10, wherein the subject is further administered one or more therapeutic antibody selected from the group consisting of an anti-VEGF antibody, an anti-VEGFR2 antibody, and an anti-EGFR antibody.

13. A method of detecting a PD-1 protein in a sample from a patient comprising contacting an anti-PD-1 antibody to the sample and detecting the anti-PD-1 antibody bound to the PD-1 protein, wherein the anti-PD-1 antibody comprises:

a. a light chain variable domain ($V_L$) sequence comprising (1) a CDR-L1 comprising the amino acid sequence KASQDVTTAVA (SEQ ID NO:9); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain ($V_H$) sequence comprising: (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDF (SEQ ID NO:14);

b. a light chain variable domain ($V_L$) sequence comprising (1) a CDR-L1 comprising the amino acid sequence KASTDVTTAVA (SEQ ID NO:15); (2) a CDR-L2 comprising the amino acid sequence WASLRHT (SEQ ID NO:16); and (3) a CDR-L3 comprising the amino acid sequence QQHYGIPWT (SEQ ID NO:17), and a heavy chain variable domain ($V_H$) sequence comprising (1) a CDR-H1 comprising the amino acid sequence FRFSNYGMS (SEQ ID NO:18); (2) a CDR-H2 comprising the amino acid sequence TISGGGSNAY (SEQ ID NO:19); and (3) a CDR-H3 comprising the amino acid sequence TSYYYGIDF (SEQ ID NO:20);

c. a light chain variable domain (V_L) sequence comprising (1) a CDR-L1 comprising the amino acid sequence KAKQDVTTAVA (SEQ ID NO:21); (2) a CDR-L2 comprising the amino acid sequence WASTRHT (SEQ ID NO:10); and (3) a CDR-L3 comprising the amino acid sequence QQHYWIPWT (SEQ ID NO:22), and a heavy chain variable (V_H) domain sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence VSYYYGIDL (SEQ ID NO:23); or d. a light chain variable domain (V_L) sequence comprising (1) a CDR-L1 comprising the amino acid sequence KASQDVTNAVA (SEQ ID NO:24); (2) a CDR-L2 comprising the amino acid sequence WASTRHT (SEQ ID NO:10); and (3) a CDR-L3 comprising the amino acid sequence QQHYTIPWT (SEQ ID NO:11), and a heavy chain variable domain (V_H) sequence comprising (1) a CDR-H1 comprising the amino acid sequence FTFSNYGMS (SEQ ID NO:12); (2) a CDR-H2 comprising the amino acid sequence TISGGGSNIY (SEQ ID NO:13); and (3) a CDR-H3 comprising the amino acid sequence SSYYYGIDL (SEQ ID NO:25).

14. The method of claim 13, wherein the anti-PD-1 antibody is used in an immunohistochemistry assay (IHC) or an ELISA assay.

15. The anti-PD-1 antibody of claim 1, comprising a light chain sequence comprising the amino acid sequence set forth in SEQ ID NO: 2, and a heavy chain sequence comprising the amino acid sequence set forth in SEQ ID NO: 4.

16. The anti-PD-1 antibody of claim 1, comprising a light chain sequence comprising the amino acid sequence set forth in SEQ ID NO: 6, and a heavy chain sequence comprising the amino acid sequence set forth in SEQ ID NO: 8.

17. The composition of claim 6, wherein the anti-PD-1 antibody comprises a light chain sequence comprising the amino acid sequence set forth in SEQ ID NO: 2, and a heavy chain sequence comprising the amino acid sequence set forth in SEQ ID NO:4.

18. The composition of claim 6, wherein the anti-PD-1 antibody comprises a light chain sequence comprising the amino acid sequence set forth in SEQ ID NO: 6, and a heavy chain sequence comprising the amino acid sequence set forth in SEQ ID NO: 8.

* * * * *

SEQUENCE LISTING

```
<160> NUMBER OF SEQ ID NOS: 34

<210> SEQ ID NO 1
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cagctcgagg atattgtgat gacccagtct cacaaattca tgtccacatc agtaggagac     60
agggtcagca tcacctgcaa ggccagtcag gatgtgacta ctgctgtagc ctggtatcaa    120
caaaaaccag ggcaatctcc taaactactg atttactggg catccacccg gcacactgga    180
gtccctgatc gcttcacagg cagtggatct gggacagatt atactctcac catcaacagt    240
gtgcaggctg aagacctggc actttattac tgtcagcaac attacactat tccgtggacg    300
ttcggtggag gcaccaagct ggaaatcaaa cgtactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t              651

<210> SEQ ID NO 2
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Leu Glu Asp Ile Val Met Thr Gln Ser His Lys Phe Met Ser Thr
1               5                   10                  15

Ser Val Gly Asp Arg Val Ser Ile Thr Cys Lys Ala Ser Gln Asp Val
            20                  25                  30

Thr Thr Ala Val Ala Trp Tyr Gln Gln Lys Pro Gly Gln Ser Pro Lys
        35                  40                  45

Leu Leu Ile Tyr Trp Ala Ser Thr Arg His Thr Gly Val Pro Asp Arg
    50                  55                  60

Phe Thr Gly Ser Gly Ser Gly Thr Asp Tyr Thr Leu Thr Ile Asn Ser
65                  70                  75                  80

Val Gln Ala Glu Asp Leu Ala Leu Tyr Tyr Cys Gln Gln His Tyr Thr
                85                  90                  95

Ile Pro Trp Thr Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
```

```
                115                 120                 125
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
    210                 215

<210> SEQ ID NO 3
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaagtgatgt tggtggagtc tgggggaggc ttagtgaagc ctggagggtc cctgaaactc      60
tcatgtgcag cctctggatt cactttcagt aactatggca tgtcttgggt tcgccagact     120
ccggagaaga gcctggagtg gtcgcaacc attagtggtg gtggtagtaa catctactat     180
ccagacagtg tgaaggggcg attcaccatc tccagagaca tgccaagaa caacctgttc     240 ctgcaaatga gcggtctgag gtctgaggac acggccctgt attactgtgt atcgtattac     300
tatggaatag acttctgggg tcaaggaacc tcagtcaccg tctcctcggc tccaccaag     360 ggcccatcgg tcttccccct agcaccctgc tccaggagca cctccgagag cacagccgcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca agcccagcaa caccaaggtg gacaagagag ttgagtccaa atatggtccc     660
ccatgcccac catgcccagc acctgagttc ctggggggac catcagtctt cctgttcccc     720
ccaaaaccca aggacactct catgatctcc cggacccctg aggtcacgtg cgtggtggtg     780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca aagccaaagg gcagccccga    1020
gagccacagg tgtacaccct gcccccatcc caggaggaga tgaccaagaa ccaggtcagc    1080
ctgacctgcc tggtcaaagg cttctacccc agcgacatcg ccgtggagtg ggagagcaat    1140
gggcagccgg agaacaacta caagaccacg cctcccgtgc tggactccga cggctccttc    1200
ttcctctaca gcaggctaac cgtggacaag agcaggtggc aggaggggaa tgtcttctca    1260
tgctccgtga tgcatgaggc tctgcacaac cactacacac agaagagcct ctccctgtct    1320
ctgggtaaa                                                            1329

<210> SEQ ID NO 4
```

<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Glu Lys Ser Leu Glu Trp Val
        35                  40                  45

Ala Thr Ile Ser Gly Gly Gly Ser Asn Ile Tyr Tyr Pro Asp Ser Val
    50                  55                  60

Lys Gly Arg Phe Thr Ile Ser Arg Asp Asn Ala Lys Asn Asn Leu Phe
65                  70                  75                  80

Leu Gln Met Ser Gly Leu Arg Ser Glu Asp Thr Ala Leu Tyr Tyr Cys
                85                  90                  95

Val Ser Tyr Tyr Tyr Gly Ile Asp Phe Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
        420                 425                 430

Thr Gln Lys Ser Leu Ser Leu Ser Leu Gly Lys
    435                 440

<210> SEQ ID NO 5
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gacatccaga tgacccagtc tccatcctcc ctgtctgcat ctgtaggaga cagagtcacc        60
atcacttgca aggccagtca ggatgtgact actgctgtag cctggtatca gcagaaacca       120
gggaaagccc ctaagctcct gatctattgg gcatccaccc ggcacactgg ggtcccatca       180
aggttcagtg gcagtggatc tgggacagat ttcactctca ccatcagcag tctgcaacct       240
gaagattttg caacttacta ctgtcagcaa cattacacta ttccgtggac gttcggtgga       300
ggcaccaagc tggaaatcaa acgtactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                          642

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Ile Pro Trp
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
caggtgcagc tggtggagtc tgggggaggc ttggtcaagc ctggagggtc cctgagactc      60
tcctgtgcag cctctggatt cactttcagt aactatggca tgtcttggat ccgccaggct     120
ccagggaagg gctggagtg gtttcaacc attagtggtg gtggtagtaa catctactac      180
gcagactctg tgaagggccg attcaccatc tccagggaca cgccaagaa ctcactgtat     240 ctgcaaatga acagcctgag agccgaggac acggctgtgt attactgtgt atcgtattac     300
tatggaatag acttctgggg tcaaggaacc tcagtcaccg tctcctcggc ctccaccaag     360
ggcccatcgg tcttccccgct agcacccctgc tccaggagca cctccgagag cacagccgcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cgaagaccta cctgcaac      600 gtagatcaca agcccagcaa caccaaggtg gacaagagag ttgagtccaa atatggtccc     660
ccatgcccac catgcccagc acctgagttc ctgggggac atcagtctt cctgttcccc      720 ccaaaaccca aggacactct catgatctcc cggaccctg aggtcacgtg cgtggtggtg      780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca aagccaaagg gcagccccga    1020
gagccacagg tgtacaccct gcccccatcc caggaggaga tgaccaagaa ccaggtcagc    1080
ctgacctgcc tggtcaaagg cttctacccc agcgacatcg ccgtggagtg ggagagcaat    1140
gggcagccgg agaacaacta caagaccacg cctcccgtgc tggactccga cggctccttc    1200
ttcctctaca gcaggctaac cgtggacaag agcaggtggc aggaggggaa tgtcttctca    1260
tgctccgtga tgcatgaggc tctgcacaac cactacacac agaagagcct ctccctgtct    1320
ctgggtaaa                                                            1329
```

```
<210> SEQ ID NO 8
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Ile Arg Gln Ala Pro Gly Lys Gly Leu Glu Trp Val
        35                  40                  45

Ser Thr Ile Ser Gly Gly Gly Ser Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Tyr Tyr Tyr Gly Ile Asp Phe Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Ala Ser Gln Asp Val Thr Thr Ala Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Ala Ser Thr Arg His Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln His Tyr Thr Ile Pro Trp Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Thr Phe Ser Asn Tyr Gly Met Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ile Ser Gly Gly Gly Ser Asn Ile Tyr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ser Tyr Tyr Tyr Gly Ile Asp Phe
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ala Ser Thr Asp Val Thr Thr Ala Val Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ala Ser Leu Arg His Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln His Tyr Gly Ile Pro Trp Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Arg Phe Ser Asn Tyr Gly Met Ser
1               5

<210> SEQ ID NO 19
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Ile Ser Gly Gly Gly Ser Asn Ala Tyr
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Tyr Tyr Tyr Gly Ile Asp Phe
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Lys Gln Asp Val Thr Thr Ala Val Ala
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln His Tyr Trp Ile Pro Trp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Ser Tyr Tyr Tyr Gly Ile Asp Leu
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ala Ser Gln Asp Val Thr Asn Ala Val Ala
```

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ser Ser Tyr Tyr Tyr Gly Ile Asp Leu
1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

```
His His His His His His
1               5
```

<210> SEQ ID NO 27
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Leu Glu Asp Ile Val Met Thr Gln Ser His Lys Phe Met Ser Thr
1               5                   10                  15

Ser Val Gly Asp Arg Val Ser Ile Thr Cys Lys Ala Ser Gln Asp Val
            20                  25                  30

Thr Thr Ala Val Ala Trp Tyr Gln Gln Lys Pro Gly Gln Ser Pro Lys
        35                  40                  45

Leu Leu Ile Tyr Trp Ala Ser Thr Arg His Thr Gly Val Pro Asp Arg
    50                  55                  60

Phe Thr Gly Ser Gly Ser Gly Thr Asp Tyr Thr Leu Thr Ile Asn Ser
65                  70                  75                  80

Val Gln Ala Glu Asp Leu Ala Leu Tyr Tyr Cys Gln Gln His Tyr Thr
                85                  90                  95

Ile Pro Trp Thr Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205
```

Thr Lys Ser Phe Asn Arg Gly Glu Cys
    210                 215

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Ile Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 95
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro
                85                  90                  95
```

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 31
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Glu Lys Ser Leu Glu Trp Val
        35                  40                  45

Ala Thr Ile Ser Gly Gly Gly Ser Asn Ile Tyr Tyr Pro Asp Ser Val
    50                  55                  60
```

Lys Gly Arg Phe Thr Ile Ser Arg Asp Asn Ala Lys Asn Asn Leu Phe
65                  70                  75                  80

Leu Gln Met Ser Gly Leu Arg Ser Glu Asp Thr Ala Leu Tyr Tyr Cys
            85                  90                  95

Val Ser Tyr Tyr Gly Ile Asp Phe Trp Gly Gln Gly Thr Ser Val
        100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Val Asp His Lys Pro Ser Asn Thr Lys Val
145                 150                 155                 160

Asp Lys Arg Val Glu Ser Lys Tyr Gly Pro Pro Cys Pro Pro Cys Pro
                165                 170                 175

Ala Pro Glu Phe Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser Gln Glu Asp Pro Glu Val Gln Phe Asn Trp Tyr
    210                 215                 220

Val Asp Gly Val Glu Val His Asn Ala Lys Thr Lys Pro Arg Glu Glu
225                 230                 235                 240

Gln Phe Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Gly Leu Pro Ser Ser Ile Glu Lys Thr Ile Ser Lys Ala Lys Gly Gln
        275                 280                 285

Pro Arg Glu Pro Gln Val Tyr Thr Leu Pro Pro Ser Gln Glu Glu Met
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Arg Leu Thr Val Asp Lys Ser Arg Trp Gln Glu Gly Asn Val
        355                 360                 365

Phe Ser Cys Ser Val Met His Glu Ala Leu His Asn His Tyr Thr Gln
    370                 375                 380

Lys Ser Leu Ser Leu Ser Leu Gly Lys
385                 390

<210> SEQ ID NO 32
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr

```
            20                  25                  30
Gly Met Ser Trp Ile Arg Gln Ala Pro Gly Lys Gly Leu Glu Trp Val
         35                  40                  45

Ser Thr Ile Ser Gly Gly Ser Asn Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Val Ser Tyr Tyr Tyr Gly Ile Asp Phe Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
        130                 135                 140

Val Lys Asp Tyr Phe Pro Val Asp His Lys Pro Ser Asn Thr Lys Val
145                 150                 155                 160

Asp Lys Arg Val Glu Ser Lys Tyr Gly Pro Pro Cys Pro Pro Cys Pro
                165                 170                 175

Ala Pro Glu Phe Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
            195                 200                 205

Val Val Asp Val Ser Gln Glu Asp Pro Glu Val Gln Phe Asn Trp Tyr
210                 215                 220

Val Asp Gly Val Glu Val His Asn Ala Lys Thr Lys Pro Arg Glu Glu
225                 230                 235                 240

Gln Phe Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Gly Leu Pro Ser Ser Ile Glu Lys Thr Ile Ser Lys Ala Lys Gly Gln
            275                 280                 285

Pro Arg Glu Pro Gln Val Tyr Thr Leu Pro Pro Ser Gln Glu Glu Met
            290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Arg Leu Thr Val Asp Lys Ser Arg Trp Gln Glu Gly Asn Val
            355                 360                 365

Phe Ser Cys Ser Val Met His Glu Ala Leu His Asn His Tyr Thr Gln
            370                 375                 380

Lys Ser Leu Ser Leu Ser Leu Gly Lys
385                 390

<210> SEQ ID NO 33
<211> LENGTH: 98
<212> TYPE: PRT
<213> ORGANISM: Homo sapiens

<400> SEQUENCE: 33
```

-continued

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 34
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Val Asp His Lys Pro Ser Asn Thr Lys Val Asp Lys Arg Val
145                 150                 155                 160

Glu Ser Lys Tyr Gly Pro Pro Cys Pro Pro Cys Pro Ala Pro Glu Phe
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
        195                 200                 205

Ser Gln Glu Asp Pro Glu Val Gln Phe Asn Trp Tyr Val Asp Gly Val
    210                 215                 220

Glu Val His Asn Ala Lys Thr Lys Pro Arg Glu Glu Gln Phe Asn Ser
225                 230                 235                 240

Thr Tyr Arg Val Val Ser Val Leu Thr Val Leu His Gln Asp Trp Leu
                245                 250                 255
```

```
-continued

Asn Gly Lys Glu Tyr Lys Cys Lys Val Ser Asn Lys Gly Leu Pro Ser
            260                 265                 270

Ser Ile Glu Lys Thr Ile Ser Lys Ala Lys Gly Gln Pro Arg Glu Pro
        275                 280                 285

Gln Val Tyr Thr Leu Pro Pro Ser Gln Glu Glu Met Thr Lys Asn Gln
        290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Arg Leu
            340                 345                 350

Thr Val Asp Lys Ser Arg Trp Gln Glu Gly Asn Val Phe Ser Cys Ser
            355                 360                 365

Val Met His Glu Ala Leu His Asn His Tyr Thr Gln Lys Ser Leu Ser
    370                 375                 380

Leu Ser Leu Gly Lys
385
```